US011261427B1

(12) United States Patent
Mao et al.

(10) Patent No.: US 11,261,427 B1
(45) Date of Patent: Mar. 1, 2022

(54) HIGHLY ORDERED PHAGE STRUCTURES AND USES THEREOF FOR STEM CELL DIFFERENTIATION

(71) Applicant: The Board of Regents of the University of Oklahoma, Norman, OK (US)

(72) Inventors: Chuanbin Mao, Norman, OK (US); Ningyun Zhou, Columbia, MD (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/975,635

(22) PCT Filed: Apr. 10, 2020

(86) PCT No.: PCT/US2020/027586
§ 371 (c)(1),
(2) Date: Aug. 25, 2020

(87) PCT Pub. No.: WO2020/210571
PCT Pub. Date: Oct. 15, 2020

Related U.S. Application Data

(60) Provisional application No. 62/832,954, filed on Apr. 12, 2019.

(51) Int. Cl.
*C12N 5/0797* (2010.01)
*C12N 7/00* (2006.01)

(52) U.S. Cl.
CPC ............ *C12N 5/0623* (2013.01); *C12N 7/00* (2013.01); *C12N 2506/45* (2013.01);
(Continued)

(58) Field of Classification Search
None
See application file for complete search history.

(56) References Cited

U.S. PATENT DOCUMENTS

2011/0197711 A1   8/2011   Belcher et al.
2011/0311490 A1   12/2011  Lee et al.
(Continued)

OTHER PUBLICATIONS

Dogic, Z., et al.; "Smectic Phase in a Colloidal Suspension of Semiflexible Virus Particles"; Physical Review Letters 78:12 (1997) 2417-2420.
(Continued)

*Primary Examiner* — Teresa E Knight
(74) *Attorney, Agent, or Firm* — Hall Estill Law Firm

(57) ABSTRACT

A bacteriophage structure, a method of making the structure, and uses of the structure are described. The structure is a substrate with a surface having an ordered arrangement of parallel microridges thereon. Each microridge is composed of a plurality of nanoridges and has a longitudinal axis. Each nanoridge contains a bundle of phage nano fibers having longitudinal axes. The phage nanofibers in each nanoridge bundle are arranged in a substantially smectic alignment. The longitudinal axis of each microridge is perpendicular to the longitudinal axes of the phage nanofibers which make up the nanoridges of the microridge. The structure may be used as a growth surface for inducing differentiation of stem cells such as neural progenitor cells.

17 Claims, 17 Drawing Sheets

(52) U.S. Cl.
CPC ...... *C12N 2533/32* (2013.01); *C12N 2533/90* (2013.01); *C12N 2535/00* (2013.01); *C12N 2795/00021* (2013.01); *C12N 2795/00031* (2013.01)

(56) References Cited

U.S. PATENT DOCUMENTS

| | | |
|---|---|---|
| 2014/0030699 A1 | 1/2014 | Weiss et al. |
| 2014/0199360 A1 | 7/2014 | Donlan et al. |
| 2018/0203026 A1 | 7/2018 | Mao et al. |
| 2019/0024042 A1* | 1/2019 | Yoo .................. C12N 5/0654 |

OTHER PUBLICATIONS

Uchida, N., et al.; "Direct isolation of human central nervous system stem cells"; PNAS 97:26 (2000) 14720-14725.

Weissman, I.L.; "Translating Stem and Progenitor Cell Biology to the Clinic: Barriers and Opportunities"; Science 287 (2000) 1442-1446.

Mao, C., et al.; "Viral assembly of oriented quantum dot nanowires"; PNAS 100:12 (2003) 6946-6951.

Mao, C., et al.; "Virus-Based Toolkit for the Directed Synthesis of Magnetic and Semiconducting Nanowires"; Science 303 (2004) 213-217.

Li, X-J, et al.; "Specification of motoneurons from human embryonic stem cells"; Nature Biotechnology 23:2 (2005) 215-221.

Dogic, Z., et al.; "Ordered phases of filamentous viruses"; Current Opinion in Colloid & Interface Science 11 (2006) 47-55.

Maragakis, N.J., et al.; "Mechanisms of Disease: astrocytes in neurodegenerative disease"; Nature Clinical Practice Neurology 2:12 (2006) 679-689.

Purdy, K.R., et al.; "Influence of charge and flexibility on smectic phase formation in filamentous virus suspensions" Physical Review 76, 011705 (2007) 1-8.

Rong, J., et al.; "Oriented cell growth on self-assembled bacteriophage M13 thin films"; Chem Commun. (2008) 5185-5187.

Edited by Sills, J.; "Letters"; Science 322 (2008) 43-46.

Allaman, I., et al.; "Amyloid-B Aggregates Cause Alterations of Astrocytic Metabolic Phenotype: Impact on Neuronal Viability"; The Journal of Neuroscience 30:9 (2010) 3326-3338.

Lee, M.R., et al.; "Direct differentiation of human embryonic stem cells into selective neurons on nanoscale ridge/groove pattern arrays"; Biomaterials 31 (2010) 4360-4366.

Wang, F., et al.; "Bacteriophage Bundles with Pre-Aligned Ca2+ Initiate the Oriented Nucleation and Growth of Hydroxylapatite"; Chem Mater. 22:12 (2010) 3630-3636.

Branston, S, et al.; "Precipitation of Filamentous Bacteriphages for Their Selective Recovery in Primary Purification"; Biotechnol. Prog. 28:1 (2012) 129-136.

Chung, W-J, et al.; "Biomimetic self-templating supramolecular structures"; Nature 478 (2011) 364-368.

Yao, H-B, et al.; "Hierarchical assembly of micro-/nano-building blocks: bio-inspired rigid structural functional materials"; Chem. Soc. Rev. 40 (2011) 3764-3785.

Moe, A.A.K., et al.; "Microarray with Micro- and Nanotopographies Enables Identification of the Optimal Topography for Directing the Differentiation of Primary Murine Neural Progenitor Cells"; Small 8:19 (2012) 3050-3061.

Yamanaka, S.; "Induced Pluripotent Stem Cells: Past, Present, and Future"; Cell Stem Cell 10 (2012) 678-684.

Ankam, S., et al.; "Substrate topography and size determine the fate of human embryonic stem cells to neuronal or glial lineage"; Acta Biomaterialia 9 (2013) 4535-4545.

Branston, S.D., et al.; "Determination of the Survival of Bacteriophage M13 from Chemical and Physical Challenges to Assist in Its Sustainable Bioprocessing"; Biotechnology and Bioprocess Engineering 18 (2013) 560-566.

Cao, B., et al.; "A general approach to controlled alignment of filamentous supra-biomolecular assemblies into centimeter-scale highly-ordered patterns through nature-inspired magnetic guidance"; Angew Chem Int Ed Engl. 52:45 (2013) 11750-11754.

Chan, L.Y., et al.; "Temporal application of topography to increase the rate of neural differentiation from human pluripotent stem cells"; Biomaterials 34 (2013) 382-392.

Pan, F., et al.; "Topographic effect on human induced pluripotent stem cells differentiation towards neuronal lineage" Biomaterials 34 (2013) 8131-8139.

Shaltouki, A., et al.; "Efficient General of Astrocytes from Human Pluripotent Stem Cells in Defined Conditions" Stem Cells 31 (2013) 941-952.

Wang, J., et al.; "Virus activated artificial EMC induces the osteoblastic differentiation of mesenchymal stem cells without osteogenic supplements"; Scientific Reports 3:1242 (2013) 1-8.

Yang, K., et al.; "Nanotopographical Manipulation of Focal Adhesion Formation for Enhanced Differentiation of Human Neural Stem Cells"; ACS Appl. Mater. Interfaces 5 (2013) 10529-10540.

Blumenthal, N.R., et al.; "Stochastic nanoroughness modulates neuron-astrocyte interactions and funtion via mechanosensing cation channels"; PNAS 111:45 (2014) 16124-16129.

Sun, Y., et al.; "Hippo/YAP-mediated rigidity-dependent motor neuron differentiation of human pluripotent stem cells" Nature Materials 13 (2014) 599-604.

Wang, J., et al.; "Untangling the Effects of Peptide Sequences and Nanotopographies in a Biomimetic Niche for Directed Differentiation of iPSCs by Assemblies of Genetically Engineered Viral Nanofibers"; Nano Lett. 14 (2014) 6850-6856.

Chapman, C.A.R., et al.; "Nanoporous Gold as a Neural Interface Coating: Effects of Topography, Surface Chemistry and Feature Size"; ACS Appl. Mater. Interfaces 7 (2015) 7093-7100.

Tiryaki, V.M., et al.; "Differentiation of reactive-like astrocytes cultured on nanofibrillar and comparative culture surfaces"; Nanomedicine 10:4 (2015) 529-545.

Wang, Y., et al.; "Ultrasensitive Rapid Detection of Human Serum Antibody Biomarkers by Biomarker-Capturing Viral Nanofibers"; ACS Nano 9:4 (2015) 4475-4483.

Cao, B., et al.; "Phage as a Genetically Modifiable Supramacromolecule in Chemistry, Materials and Medicine"; Acc Chem Res. 49:6 (2016) 1111-1120.

Song, L., et al.; "Nanotopgraphy promoted neuronal differentiation of human induced pluripotent stem cells"; Colloids and Surfaces B: Biointerfaces 148 (2016) 49-58.

TCW, J., et al.; "An Efficient Platform for Astrocyte Differentiation from Human Induced Pluripotent Stem Cells"; Stem Cell Reports 9 (2017) 600-614.

Gunhanlar, N., et al.; "A simplified protocol for differentiation of electrophysiologically mature neuronal networks from human induced pluripotent stem cells"; Molecular Psychiatry 23 (2018) 1336-1344.

Lin, C., et al.; "Interaction of iPSC-derived neural stem cells on poly(L-lactic acid) nanofibrous scaffolds for possible use in neural tissue engineering"; International Journal of Molecular Medicine 41 (2018) 697-708.

Que, R.A., et al.; "Recombinant collagen scaffolds as substrates for human neural stem/progenitor cells"; Journal of Biomedical Materials Research 106A:5 (2018) 1363-1372.

Seuring, C., et al.; "Femtosecond X-ray coherent diffraction of aligned amyloid fibrils on low background graphene" Nature Communication 9:1836 (2018) 1-10.

Yang, J., et al.; "Engineering Surface and Optical Properties of TiO2-Coated Electrospun PVDF Nanofibers Via Controllable Self-Assembly"; Nanomaterials 8:741 (2018) 1-17.

He, C., et al.; "Bioinspired Shear-Flow-Driven Layer-by-Layer in Situ Self-Assembly"; ACS Nano 13 (2019) 1910-1922.

Patel, B.B., et al.; "3D Microfibrous Scaffolds Selectively Promotes Proliferation and Glial Differentiation of Adult Neural Stem Cells: A Platform to Tune Cellular Behavior in Neural Tissue Engineering"; Macromol. Biosci. 19, 1800236 (2019) 1-13.

Zhou, N., et al.; "Hierarchical Ordered Assembly of Genetically Modifiable Viruses into Nanoridge-in-Microridge Structures"; Advanced Materials 31:52 (2019) 3 pages (abstract only).

(56) References Cited

OTHER PUBLICATIONS

Liu, L., et al.; "Three-dimensional brain-on-chip model using human iPSC-derived GABAergic neurons and astrocytes Butyrylcholinesterase post-treatment for acute malathion exposure"; PLOS ONE (2020) 1-13.

PCT/US2020/027586 "International Search Report and Written Opinion"; dated Jul. 6, 2020; 7 pages.

\* cited by examiner

HIGHLY ORDERED PHAGE STRUCTURES AND USES THEREOF FOR STEM CELL DIFFERENTIATION

CROSS REFERENCE TO RELATED APPLICATIONS

The present application is a national stage application of a PCT application having International Application No. PCT/US2020/027586, filed Apr. 10, 2020, which claims priority to U.S. Provisional Application having U.S. Ser. No. 62/832,954, filed Apr. 12, 2019, which claims the benefit under 35 U.S.C. 119(e), the disclosure of which is hereby expressly incorporated herein by reference.

BACKGROUND

Patients with neurodegenerative diseases (NDDs) such as Parkinson's disease and Alzheimer's disease experience troubles with memory, walking, speaking, and mood. There are many possible causes of NNDs, including genetic mutation and heritages, toxic intercellular environment, organelle damages, and axonal dysfunction. These causes all result in the loss of structures and functions of neurons and astrocytes and even their death. Both neurons and astrocytes are the building blocks of the human brain and thus are needed simultaneously in treating NDDs. Neurons are the most important cell types in the central nervous system (CNS). They can convey the information to each other by chemical and electrical signals through synapses. When neurons are damaged, they cannot be regenerated by themselves, leading to the NDDs. Astrocytes, the most abundant among glial cells, are usually considered as a supportive part in the CNS. They provide the nutrients for neuron growth, the structural and metabolic supports for neurons, maintain the extracellular environment, and are in charge of the neuron-astrocyte communications. In other words, the survival of the neurons is depended on the astrocytes. In addition, astrocytes promote the neuronal differentiation and regulate the synapses generation of a neuron in the neuronal development process. Thus, the presence of both neurons and astrocytes and their interactions are important for maintaining normal CNS activities and for treating NDDs such as Alzheimer's disease (AD) and Parkinson's disease (PD).

Hence, there is a pressing need to simultaneously regenerate both neurons and astrocytes to advance the NDD treatment and to generate a coculture model for studying the interactions between both cells. Computational digital implementation modeling and neuron-astrocyte coculture were used to study the neuron-astrocyte interactions. So far, there have been very limited studies on the use of nanomaterials to generate a neuron-astrocyte coculture model. The main drawback of these studies lies in their use of rat cells to generate the neuron-astrocyte co-culture. Though the rat cells functioned similar to human cells, human cells will be more reliable when it comes to developing seed cells for treating the NDDs. There are some coculture methods involved in rodent astrocytes and human neuronal cells. However, those cells are from different sources and may cause incompatibility. Thus, generating neurons and astrocytes from the same human cell source will facilitate both the development of NDD treatment strategies and the generation of neuron-astrocyte coculture models.

Stem cells have the ability to differentiate into many types of cells. They can be used to solve the problem associated with the species difference in the traditional coculture method and are a new promising cell source to cure NDDs. Adult neural stem cells (NSCs) or adult neural progenitor cells (NPCs) are the direct source for neural differentiation, but both cells can only be isolated from normal human brain which is hard to get. Human induced pluripotent stem cells (hiPSCs) are one of the new cell sources for tissue regeneration. They can differentiate into all types of cells and thus used to develop patient-specific stem cell therapy while avoiding ethical issues. Nowadays, hiPSCs based stem cell therapy has become one of the most promising NDD treatments. The behaviors of hiPSCs, especially their differentiation, were strongly influenced by their microenvironment. A material can serve as a matrix for providing such microenvironment to modulate their differentiation. However, so far, a material has used to generate either neurons or astrocytes from hiPSCs, and, to the best of our knowledge, no structural material has been used to achieve the regeneration of both neurons and astrocytes from a human cell source such as hiPSCs although both cells are needed for treating NDDs.

BRIEF DESCRIPTION OF THE DRAWINGS

Several non-limiting embodiments of the present disclosure are hereby illustrated in the appended drawings. It is to be noted, however, that the appended drawings only illustrate several embodiments and are therefore not intended to be considered limiting of the scope of the present disclosure. This patent or application file contains at least one drawing executed in color. Copies of this patent or patent application publication with color drawing(s) will be provided by the Office upon request and payment of the necessary fee.

DETAILED DESCRIPTION

Figure 1:
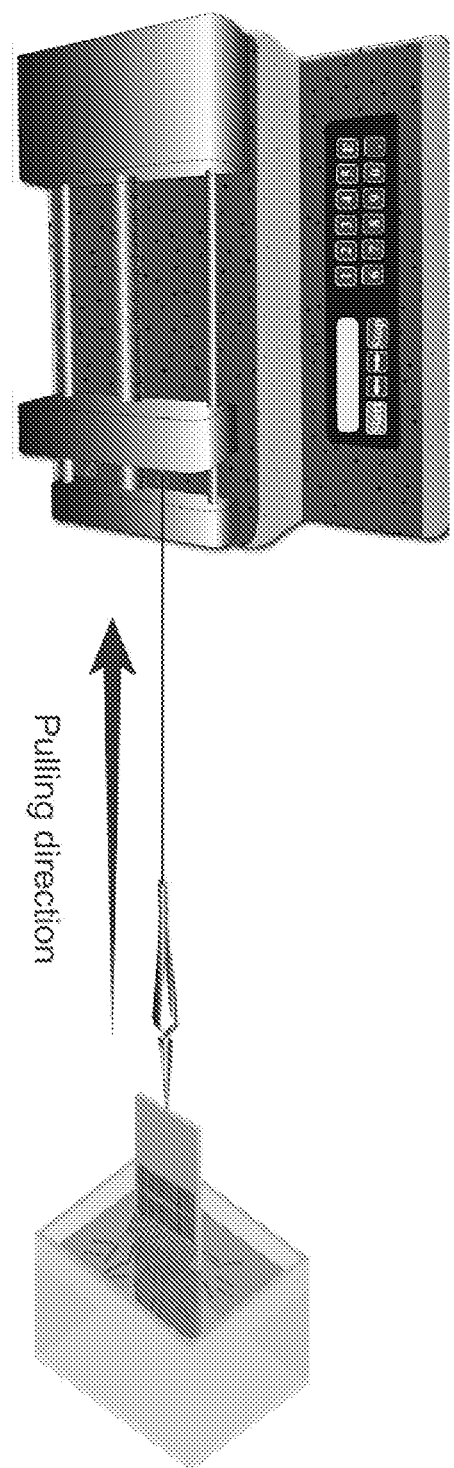
FIG. 1 shows a schematic illustration of a dip-pulling method used to cause self-assembly of phages on substrates into hierarchical nanoridge-in-microridge (NiM) structures. Arrows denote the pulling force direction. Also indicated is an illustration showing a single filamentous phage.

The present disclosure is directed to a novel highly ordered biomolecular material constructed on a substrate surface assembled from filamentous bacteriophages ("phages") using a dip-pulling process. This highly ordered phage structure, also referred to herein as a nanoridge-in-microridge (NiM) structure (or phage scaffold), can then be used as a surface to induce the bidirectional differentiation of stem cells such as neural progenitor cells (NPCs) derived from human induced pluripotent cells (hiPSCs). In the case of NPCs the cells differentiate into both neurons and astrocytes in the absence of additional differentiation inducers in the culture medium. In one non-limiting embodiment, the filamentous phage M13 may be used. M13 phage is a human-safe viral nanofiber that is made of a sheath of coat proteins encapsulating a circular ssDNA. The side wall of the phage nanofiber is assembled from ~3000 copies of a major coat protein (termed p8).

Before further describing various embodiments of the structures, compositions and methods of the present disclosure in more detail by way of exemplary description, examples, and results, it is to be understood that the embodiments of the present disclosure are not limited in application to the details of structures, methods and compositions as set forth in the following description. The embodiments of the structures, compositions and methods of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the compositions and methods of the present disclosure have been described in terms of particular embodiments, it will be apparent to those of skill in the art that variations may be applied to the structures, compositions and/or methods and in the steps or in the sequence of steps of the method described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification, including U.S. Provisional Patent Application Ser. No. 62/832,954, filed on Apr. 12, 2019, are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" and "approximately" are used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, percentage, temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described object, event or circumstance completely occurs or that the subsequently described object, event or circumstance occurs to a great extent or degree. For example, the term "substantially" means that the subsequently described object, event or circumstance occurs at least 80% of the time, and more particularly at least 90% of the time, at least 95% of the time, or at least 98% of the time. Where used herein in regard to phage nanofibers in nanoridges, the term "substantially parallel to one another" generally means that at least 80% of phage nanofibers in a bundle in a nanoridge are aligned in a parallel orientation, and more particularly at least 90% of the phage nanofibers are aligned in a parallel orientation. Where used herein in reference to phage nanofibers in a nanoridge, the term "parallel" means that two phage nanofibers have no more than a 15 degree angle therebetween.

Where used herein the term "smectic" refers to the arrangement of phage nanofibers in layers with the longitudinal axes in a given layer parallel to one another. Herein, bundles of such smectically-aligned phage nanofibers are referred to as nanoridges. A plurality of such nanoridges in a line together form a microridge.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. The range 1 (unit) to 100 (units) is intended to include any sub-range therein, although that sub-range may not be explicitly designated herein. For example, since the range 1 to 100 includes all integers from 1 to 100, the sub-ranges therein include any range having a minimum value of 1 unit and any maximum value of 100 units, such as but not limited to, 5 to 75 units, 10 to 50 units, or 15 to 40 units. Thus, to further illustrate a series of ranges, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 100 units to 2000 units therefore refers to and includes all values or ranges of values of the units, and fractions of the values of the units and integers within said range, including for example, but not limited to 100 units to 1000 units, 100 units to 500 units, 200 units to 1000 units, 300 units to 1500 units, 400 units to 2000 units, 500 units to 2000 units, 500 units to 1000 units, 250 units to 1750 units, 250 units to 1200 units, 750 units to 2000 units, 150 units to 1500 units, 100 units to 1250 units, and 800 units to 1200 units. Any two values within the range of about 100 units to about 2000 units therefore can be used to set the lower and upper boundaries of a range in accordance with the embodiments of the present disclosure.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability of an active agent to modify the physiological system of an organism without reference to how the active agent has its physiological effects.

As used herein, "pure," "substantially pure," or "isolated" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure. Where used herein the term "high specificity" refers to a specificity of at least 90%, or at least 91%, or at least 92%, or at least 93%, or at least 94%, or at least 95%, or at least 96%, or at least 97%, or at least 98%, or at least 99%. Where used herein the term "high sensitivity" refers to a sensitivity of at least 90%, or at least 91%, or at least 92%, or at least 93%, or at least 94%, or at least 95%, or at least 96%, or at least 97%, or at least 98%, or at least 99%.

The following abbreviations may be used herein for amino acids: alanine:ala:A; arginine:arg:R; asparagine:asn:N; aspartic acid:asp:D; cysteine:cys:C; glutamic acid:glu:E; glutamine:gln:Q; glycine:gly:G; histidine:his:H; isoleucine:ile:I; leucine:leu:L; lysine:lys:K; methionine:met:M; phenylalanine:phe:F; proline:pro:P; serine:ser:S; threonine:thr:T; tryptophan:trp:W; tyrosine:tyr:Y; and valine:val:V.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein any reference to "we" as a pronoun herein may refer generally to personnel or other contributors who assisted in the laboratory procedures and data collection and is not intended to represent an inventorship role by said personnel or other contributors in any subject matter disclosed herein.

Returning to the detailed description, disclosed herein is a method termed dip-pulling for creating nano-to-micro hierarchical filamentous "phage-on-substrate" phage film structures (also termed nanoridge-in-microridge (NiM) structures or phage scaffolds). Also disclosed herein are methods of using the NiM structures to induce the bidirectional differentiation of stem cells, for example of neural progenitor cells (NPCs) derived from human induced pluripotent stem cells (hiPSCs) into both neurons and astrocytes. The filamentous phages used may be, for example, f1, fd, or M13 phages.

Examples

Various inventive concepts of the present disclosure will now be discussed in terms of several specific, non-limiting, examples. The examples described below, which include particular embodiments, will serve to illustrate the practice of the present disclosure, it being understood that the particulars shown are by way of example and for purposes of illustrative discussion of particular embodiments of the present disclosure only and are presented in the cause of providing what is believed to be a useful and readily understood description of construction procedures as well as of the principles and conceptual aspects of the inventive concepts.

Methods

Phage Amplification and Purification

The *E. coli* K12 ER2738 (NEB) strain and its engineered strain were used to produce both WT-phage and RGD-phage, respectively. The bacteria were incubated at 37° C. with overnight shaking. The M13K07 helper phage (NEB) was added into the overnight bacteria solution and incubated for 1 h. Then the mixture of phage and bacteria was transferred into a small flask and shaken for 3 h to allow phage to infect bacteria. Chloramphenicol antibiotics (50 µg ml$^{-1}$) was used to select the RGD-phage in this step. The product was subsequently transferred into 1 L LB broth and shaken for 24 h at 37° C. Kanamycin (70 µgm/ml) was used to select the phage infected bacteria and IPTG was used to induce RGD phagemid expression. The resultant RGD-phage or WT-phage was separated from bacteria by centrifugation. The PEG-NaCl solution (16.7% PEG/3.3 M NaCl) was added to the supernatant to induce phage precipitation at 4° C. overnight. Water was added to resuspend the precipitated phages. The above precipitation and suspension steps were repeated one more time for phage purification. The final phage solution was dialyzed against ddH$_2$O overnight for further use. A nanophotometer was used to detect the phage concentration.

Phage Film Fabrication by Dip Pulling

The poly-lysine coated glass slides or coverslips were dipped into dialyzed phage solution and pulled from the solution at different speeds, which was controlled by a syringe pump (Stoelting). In the evaporation change experiment, the normal evaporation rate was under room temperature and the fast evaporation rate was applied in the chemical fume hood. Salt concentrations of the phage solutions were adjusted by adding NaCl solution. The pH values of the phage solutions were controlled by using buffers of different pH values (Table 1). The surface structures of the resultant phage films were confirmed by an Atomic Force Microscope (Bruker) and Optical Microscope (Nikon).

TABLE 1

Buffers used for achieving different pH values.

| pH value | Buffer |
|---|---|
| 5.0 | HAc-NaAc |
| 6.0 | Na$_2$HPO$_3$-NaH$_2$PO$_3$ |
| 9.0 | Na$_2$CO$_3$-NaHCO$_3$ |
| 10.0 | Na$_2$CO$_3$-NaHCO$_3$ |
| 11.0 | Na$_2$CO$_3$ |

Pretreatment of Substrate Surface

Substrates to be used were treated to form a positively charged coating thereon. Flat substrates of gold, titanium and stainless steel were dipped in polylysine solution (0.01%) for 10 min at room temperature (RT), whereas polycarbonate plastic slide and silicon were incubated in 0.01% polylysine solution overnight at RT to form polylysine coatings. Phage film fabrication steps were the same as for glass slides.

Cell Culture

HiPSCs (cell application Inc.) were first cultured in mTeSR (Stemcell Tech.) to maintain their pluripotency. After 5-7 days, they were split into single cells and seeded on Matrigel (Corning)-coated plates for NPC differentiation. They were differentiated into NPCs according to the company's (Stemcell Tech) monolayer culture protocol. The STEMdiff™ Neural Induction Medium (Stemcell Tech) was used to differentiate hiPSCs into NPCs, which were then maintained in the STEMdiff™ Neural Progenitor Medium (Stemcell Tech). Differentiation of hiPSCs into NPCs after 21 days of culture in Neural induction medium (Stemcell Tech.) was confirmed by staining with SSEA4, a pluripotent marker, and Nestin and PAX6, NPC markers.

Cell Culture on Phage Film

Phage films were exposed to UV light for 4-6 h for sterilization. The sterilized phage films were pre-treated with laminin at 37° C. for 1 h to form laminin coating. The hiPSCs derived-NPCs were seeded on the laminin coated-phage films and cultured in the STEMdiff™ Neural Progenitor medium. The medium was changed on the daily basis.

RT-qPCR

The NPCs on the phage films were harvested at different time points (10 coverslips for each group). They were digested by accutase and then resuspended in cold PBS.

Cells ($10^5$ cells) were counted as a separate bio-repeat. The Power SYBR Green Cells-to-Ct Kit (Thermofisher) was used to perform the RealTime-qPCR. 3-4 bio-repeats were used at different time points for cells cultured on the WT-phage films, RGD-phage films and control substrate (no phage).

Immunofluorescent Staining and Intensity Analysis

Paraformaldehyde (4%) was used to fix the cells for 20 min at RT after PBS washing (3 times) steps. The cells were treated with Triton X-100 (0.3%) at RT for 5 min to allow for the penetration of the cell membrane. After penetration, BSA (10%) was used for blocking for 1 h at RT. Then, the cells were incubated with the primary antibody specific for nestin (1:200), MAP2 (1:500), GFAP (1:5000) (Abcam) and βIII-Tubulin (1:500) (Thermofisher) overnight in BSA (3%) solution. The secondary antibodies (Goat Anti-Mouse IgG H&L, Goat Anti-Chicken IgY H&L, Goat Anti-Rabbit IgG H&L) were labeled with Alexa Fluor® 488 and Alexa Fluor® 555 (Abcam). DAPI was incubated with the cells to stain the nucleus. The stained cells were fluorescently imaged. The average immunofluorescent intensity of the cells was analyzed by Image J, which was based on randomly selected ten cells in about 5 images.

Statistical Analysis

One-way ANOVA was adopted to perform statistical analysis. Different substrate groups were compared with a p value less than 0.05, 0.01, 0.001, or 0.0001 considered significantly different.

Results

HiPSCs substantially don't adhere to the phage structures (also referred to herein as phage films and NiM structures), possibly due to the formation of suspended cell clusters called embryonic bodies during their differentiation into NPCs. However, the NPCs derived from them did not form the suspended clusters but adhered well to the NiM structures. Thus the NiM structures presented a unique nanotopography upon which NPCs derived from hiPSCs could be cultured to induce bidirectional differentiation of the NPCs into neurons and astrocytes in the absence of additional differentiation inducers. The NiM structures can be formed on virtually any type of material having a positively charged coating. The general scheme and structural topography resulting from the dip-pulling to form the phage structures are shown in FIGS. 1-3.

Filamentous M13 phage is a human-safe bacteria-specific viral nanofiber that is made of a sheath of coat proteins encapsulating a circular ssDNA. The side wall of the nanofiber is assembled from ~3000 copies of a major coat protein (termed p8). Two types of M13 phage were used herein. One is the wild-type phage (termed WT-phage) and the second is a phage (termed RGD-phage herein) engineered to have RGD adhesion peptides displayed on the side wall (through fusion of RGD to N-terminal of p8 by genetic means reported in B. R. Cao, M. Y. Yang, C. B. Mao, Acc. Chem. Res. 2016, 49, 1111). Both WT-phage and RGD-phage are nanofibers (~7 nm wide) with a negatively charged protein shell. Any other suitable adhesion peptide could be used instead of RGD. The WT-phage (~1.2 µm long) is longer than RGD-phage (~550 nm long). It is known that displaying a peptide on the side wall of M13 phage shortens the phage. The present dip-pulling method was designed as a one-step operation (one dipping and one pulling) under automatic control to avoid the irreproducibility commonly seen in manual or multi-step operation. A glass slide having a positively charged coating (in this case poly-lysine) was dipped into a monodisperse phage solution, and then vertically pulled out of the solution at a stable speed automatically controlled by a syringe pump (FIG. 1).

Figure 2:
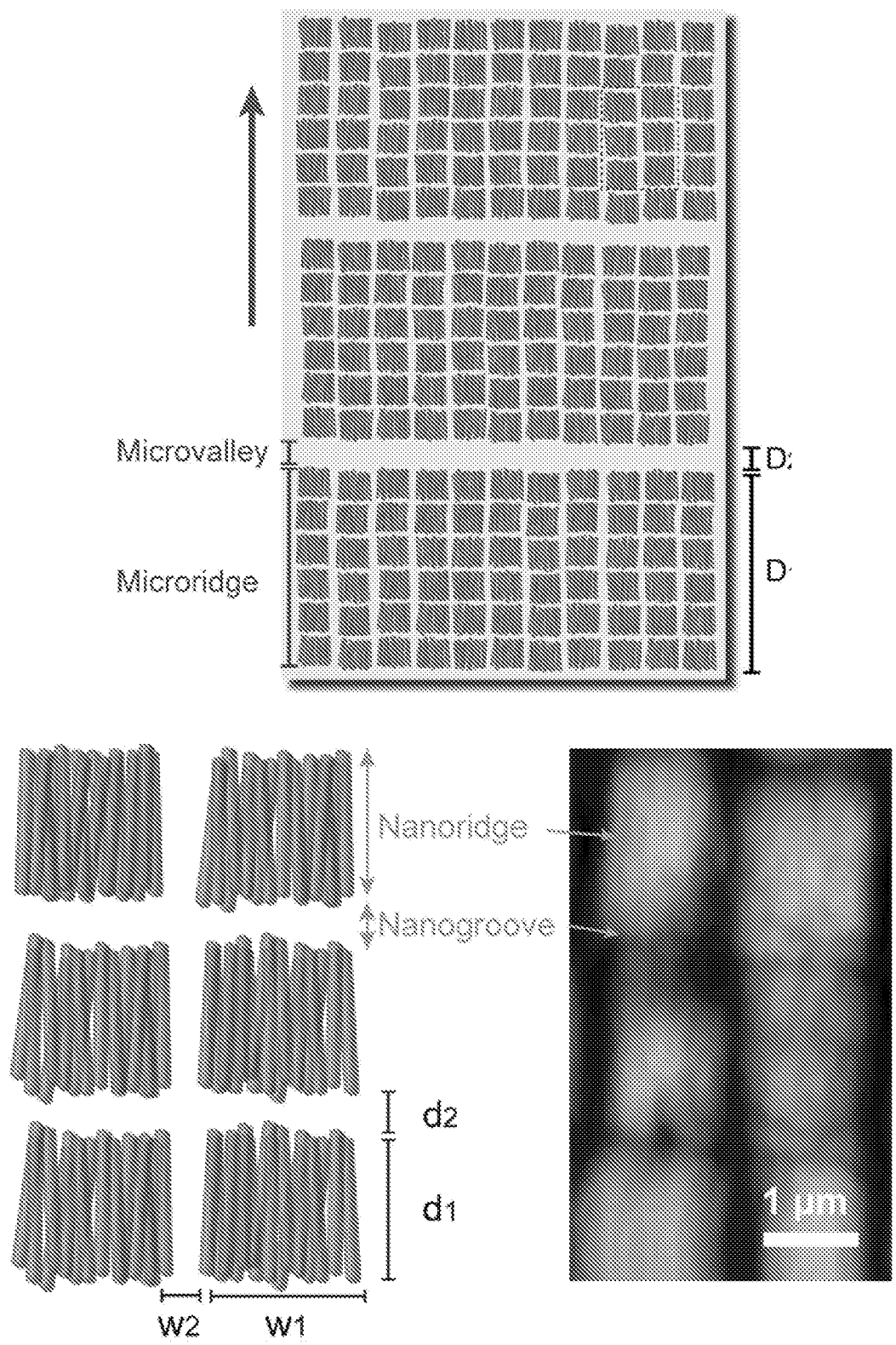
FIG. 2 shows an illustration of filamentous phages organized into nanoridges and microridges (which comprise multiple nanoridges). In the NiM structure phages are parallel to the pulling force direction and become ordered into parallel-aligned nanoridges that are further hierarchically assembled into parallel microridges that are perpendicular to the pulling force direction. The upper panel shows a front view of the NiM structure with two adjacent microridges separated by a microvalley. $D_1$ and $D_2$ are the width of microrideges and microvalleys, respectively. The lower panel shows a side view of the NiM indicating the presence of a microvalley in between microridges with the microvalley made of phage layers of decreasing thickness. The lower panel shows an illustration and a high magnification AFM image of the nanoridge and nanogroove structure. The nanoridges (having a width $d_1$) are separated by nanogrooves (having a width $d_2$). $d_1$ and $w_1$ are the length and width of the nanoridges, respectively. $d_2$ and $w_2$ are the size of the nanogrooves between the nanoridges along and perpendicular to the pulling direction, respectively. The nanoridges were organized into microridges separated by the microgrooves. Each nanoridge is just a bundle formed by parallel-aligned phages, and thus $d_1$ should be theoretically the length of a phage nanofiber. Arrows denote the pulling force direction.
Figure 3:
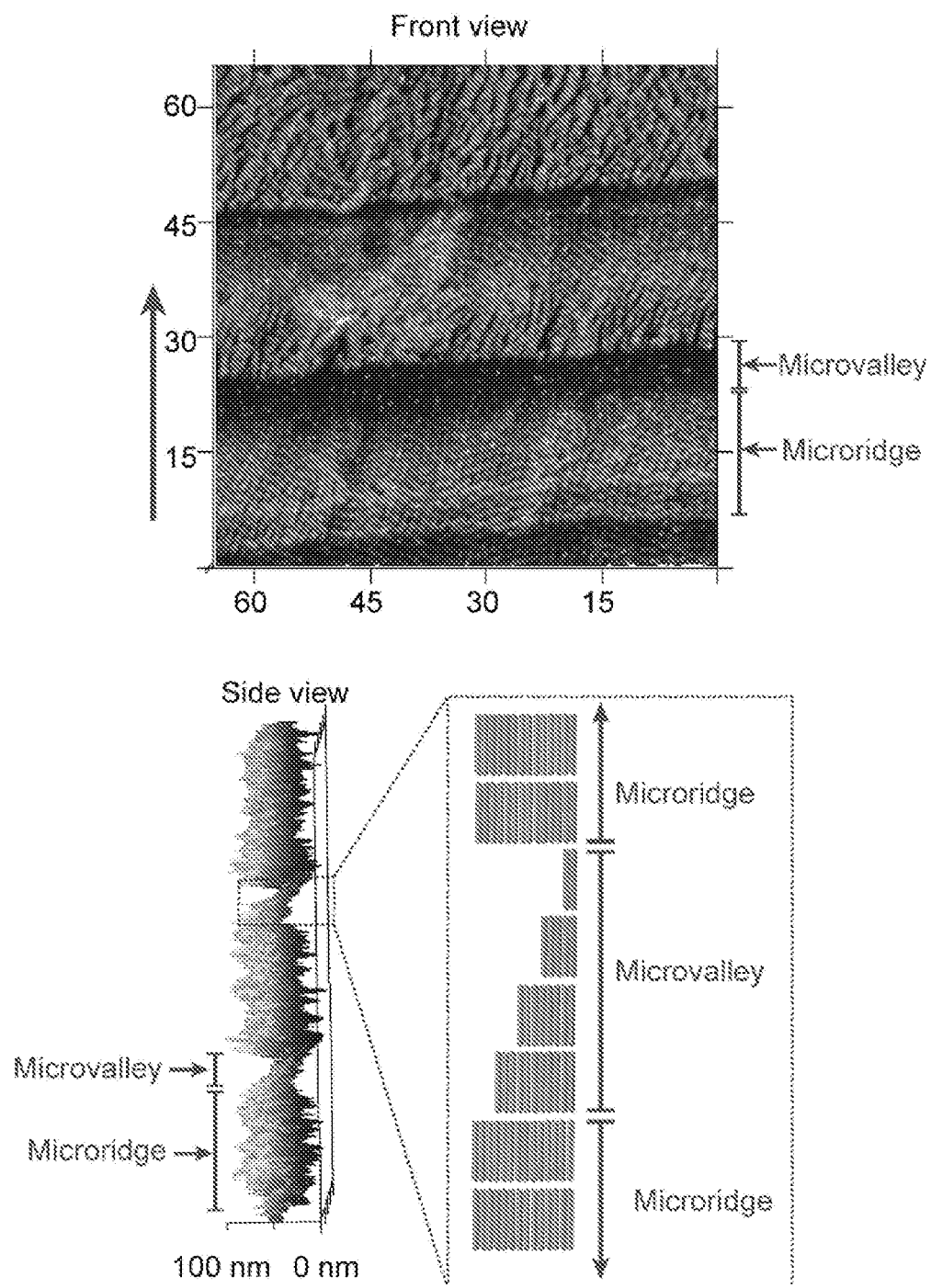
FIG. 3 shows a front view AFM image of a NiM phage film structure assembled from wild-type phages with a concentration of $1 \times 10^{14}$ plaque-forming units per milliliter (pfu/ml) by the dip-pulling method at a pulling speed of 0.5 µm/s (upper panel). Microridges and microvalleys are indicated. The lower panel shows a side view of microridges separated by microvalleys. Arrows denote the pulling force direction.

During the dip-pulling process, the positively charged coated glass slide attracted negatively charged phages to its surface and the phages were aligned in a parallel orientation to form a novel hierarchical structure termed "nanoridge-in-microridge" herein which was perpendicular to the pulling direction (FIGS. 2-3). Such NiM structure has never been reported before and is significantly different from prior reported alignments of bionanofibers (e.g., Rong et al., Chem. Commun. 2008, 5185; Chung et al., Nature 2011, 478, 364; Seuring et al., Nat. Commun. 2018, 9, 1836; Yang et al., Prog. Polym. Sci. 2018, 81, 80; Wang et a., Nano Lett. 2014, 14, 6850). The NiM pattern in the hierarchical structure appears like a window blind with each lath (the microridge) made of subunits (nanoridges assembled from parallel-aligned phages). The NiM showed a periodic pattern at both nano- and micro-structure. At the microscale, microridges comprising clusters of nanoridges were parallel to each other, with microvalleys between adjacent microridges (FIG. 2(a)). The microvalleys were made of phage bundles with decreasing thickness along the pulling direction (FIG. 3). At the nanoscale, each microridge is made of a number of stacks of parallel nanoridges separated by nanogrooves (FIG. 2 (a-b)). Each nanoridge comprises a cluster of parallel phages stacked upon each other and is as wide as the length of an individual phage. In such structure, the phages are always aligned substantially parallel to the direction of the pulling force, probably because they have the smallest hydrodynamic interactions with fluid in the shear force direction. Factors affecting the assembly of phages in a NiM structure included pulling speed, phage concentration, salt concentration (ionic strength), and pH value. Without wishing to be bound by theory, it is believed that the NiM formation mechanism is related to the solvent evaporation at the meniscus of air-fluid-solid interface moving along the pulling force. It likely that the phage solution reaches a concentration higher than the minimum concentration for forming a smectic liquid crystal phase at the meniscus.

Six size parameters for the NiM structures were defined as shown in FIG. 2. $D_1$ and $D_2$ are the widths of the microridges and microvalleys, respectively (FIG. 2(a)). $d_1$ and $w_1$ are the length and width of the nanoridges, respectively (FIG. 2(b)). $d_2$ and $w_2$ are the widths of separation of the nanogrooves between the nanoridges along and perpendicular to the pulling direction, respectively (FIG. 2(b)).

Figure 4:
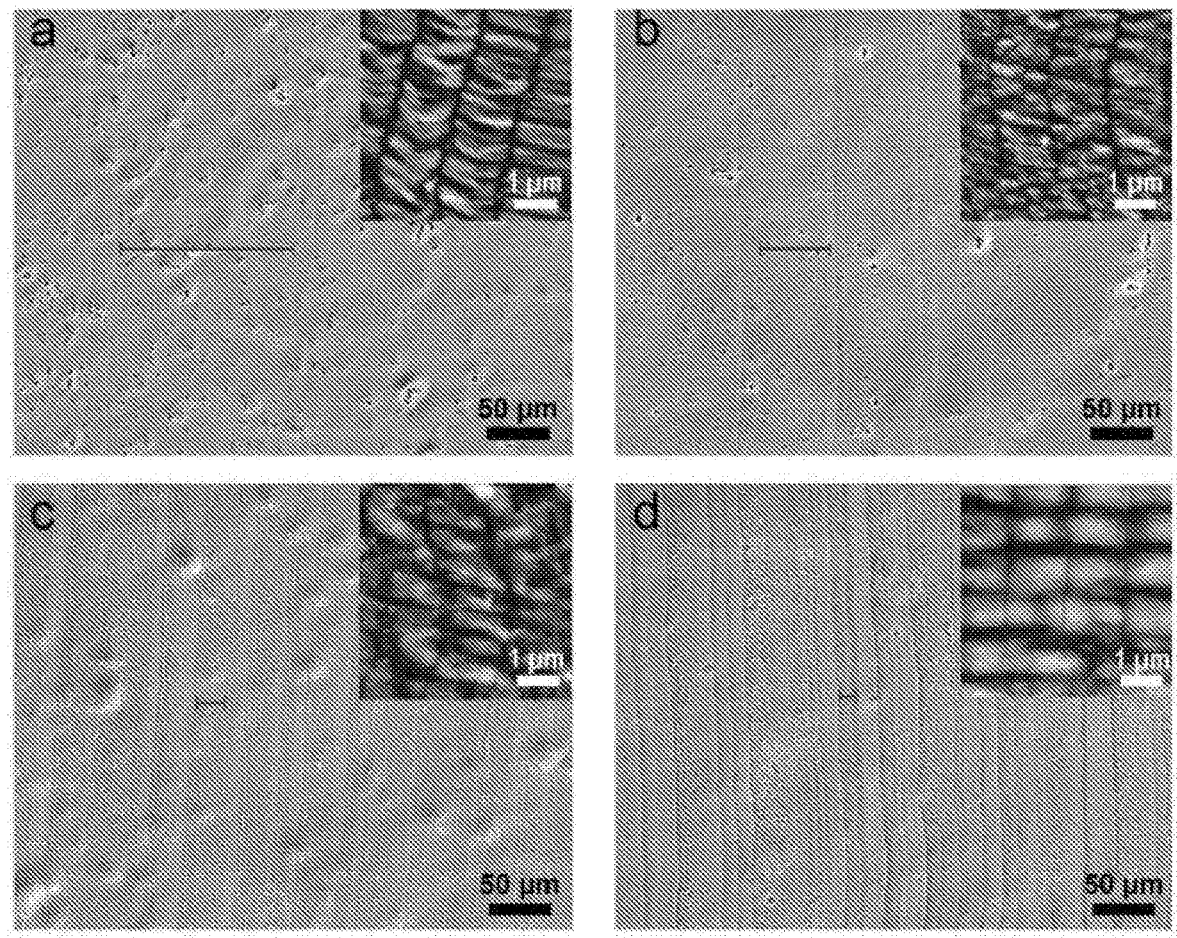
FIG. 4 shows bright field optical micrographs and AFM (inset) images of NiM structures assembled from a phage solution ($1\times10^{14}$ pfu/ml) at different pulling speeds by the dip-pulling method. The dip pulling speeds were (a) 10 µm/s, (b) 4 µm/s, (c) 1.5 µm/s, and (d) 0.5 µm/s. The bar on the images indicated the average width ($D_1$) of the microridges at each speed. As the speed is reduced, the distance between microridges became smaller.
Figure 4:

As shown in FIG. 4(a-d), NiM structures were consistently formed at different pulling speeds (10 µm/s, 4 µm/s 1.5 µm/s, and 0.5 µm/s), using a phage solution with a concentration of $1\times10^{14}$ pfu/ml), as confirmed by atomic force microscopy (AFM), although several of the size parameters of the nanoridges and microridges and the nanogrooves and microvalleys varied according to pulling speed.

Figure 5:
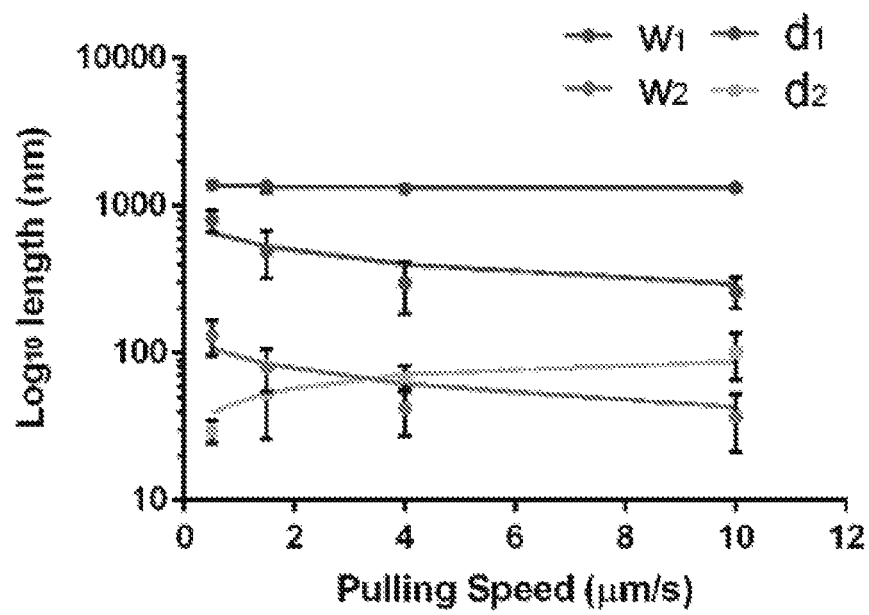
FIG. 5 shows the relationship between the pulling speed and NiM parameters $w_1$, $w_2$, $d_1$, $d_2$. The length of $d_1$ (upper curve) didn't change with the speeds because it reflects the phage length, while $d_2$ increased, and $w_1$ and $w_2$ decreased.
Figure 6:
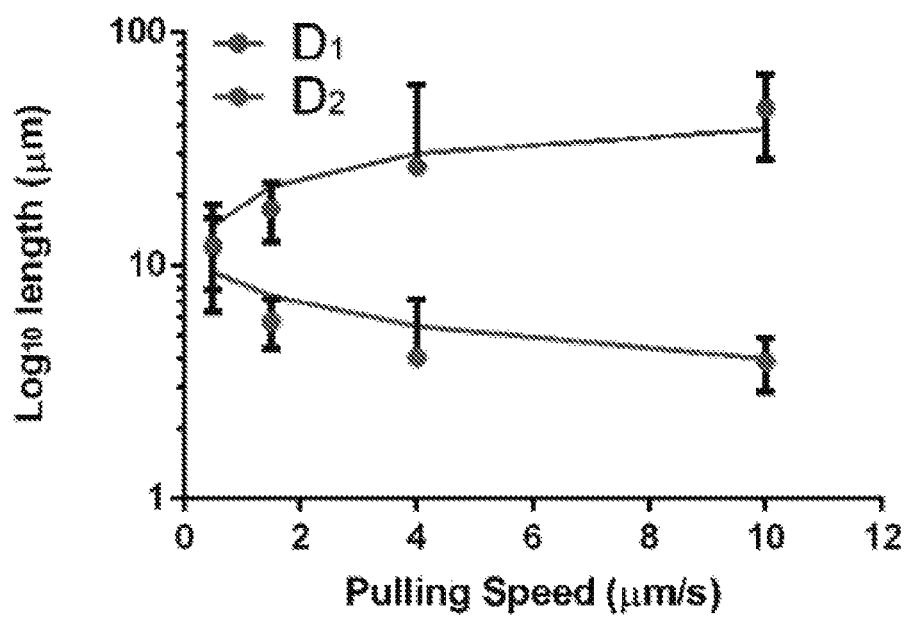
FIG. 6 shows the relationship between the pulling speed and NiM parameters $D_1$, $D_2$. As pulling speed increased $D_1$ increased (upper curve) and $D_2$ decreased (lower curve).
Figure 7:
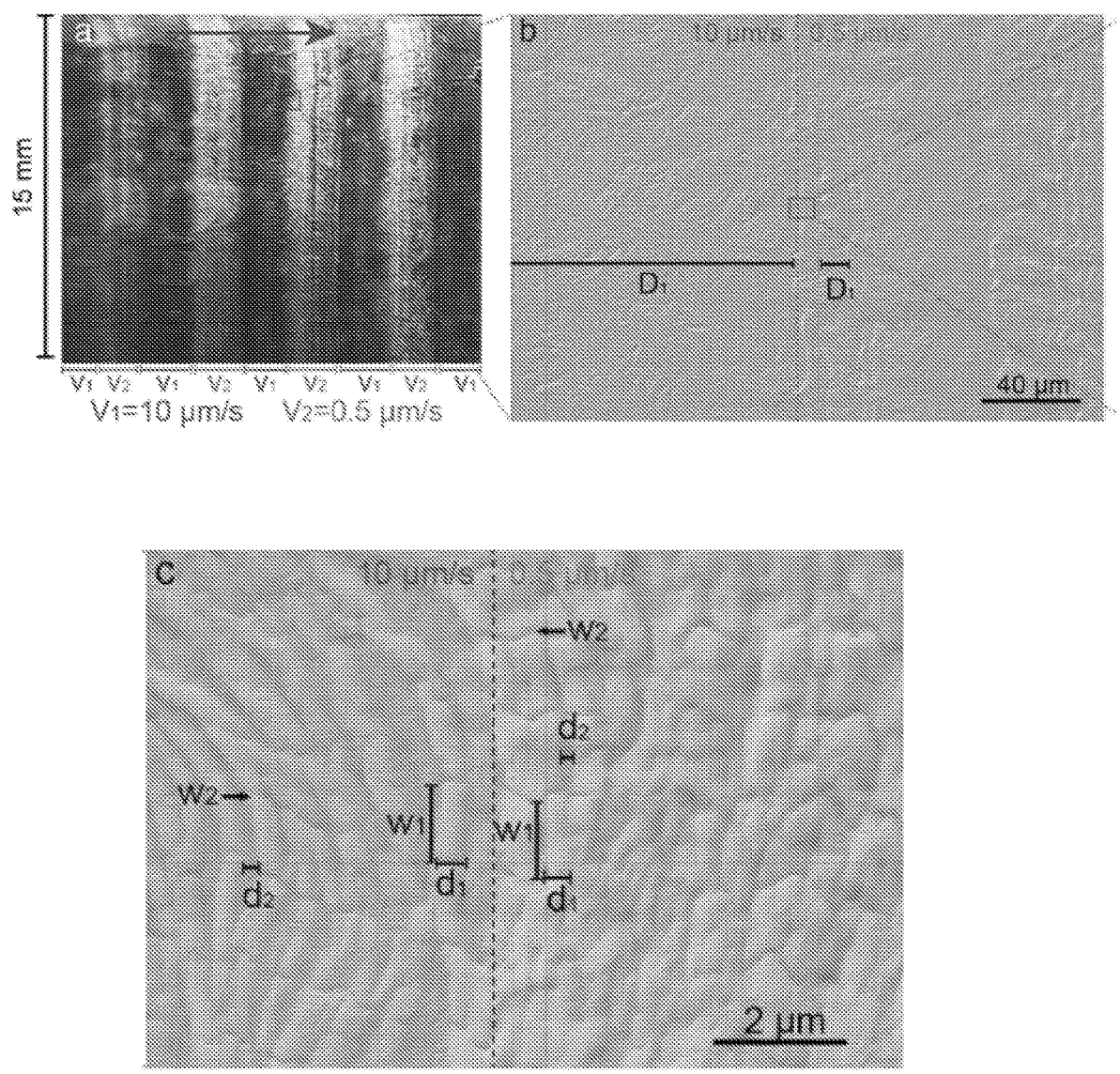
FIG. 7 shows images of RGD-phage NiM structures formation under periodic pulling speeds. (a) is an optical microscope image of a film formed when a polylysine treated glass slide was vertically pulled out of the phage solution under periodic pulling speeds (10 µm/s and 0.5 µm/s). (b) is an SEM image of the highlighted area in the rectangle in (a). (c) is an SEM image of the highlighted area in the rectangle in (b). Both (a) and (b) showed that the width $D_1$ of the microridges and width $d_2$ of the nanogrooves increased with the speed increase while other size parameters were nearly unaffected by the speed changes. In some areas of the low speed side, $d_2$ (the nanogroove size) became very small, making two neighboring nanoridges seem to be nearly linked. Dashed vertical lines indicate the speed boundaries. Arrow in (a) indicates the pulling direction. Phage concentration was $1\times10^{14}$ pfu/ml.

Because each nanoridge is actually just a cluster (bundle formed by lateral aggregation of parallel-aligned phages,) $d_1$ should be the length of a phage nanofiber. This is confirmed by our finding that $d_1$ was nearly constant and independent from the pulling speed change (FIG. 5). However, with the increase in the pulling speed, $D_1$ and $d_2$ were increasing whereas $D_2$, $w_1$ and $w_2$ were decreasing (FIGS. 5-6). The effect of periodic pulling speeds (10 µm/s and 0.5 µm/s) on the phage film formation was also studied (FIGS. 7A-C)). It was found that found that $d_1$, $w_1$, and $w_2$ were nearly not affected by the periodic speed change. However, $D_1$ and $d_2$ still followed our predicted trend under both speeds; their values on the higher speed side are larger than those on the lower speed side. On the speed boundary line, we can see a sudden change on the nanostructures when a speed was changed to another one (FIG. 7C). On the fast speed side (10 μm/s), the nanoridges tended to become bent along the pulling direction, while on the slow speed side (0.5 μm/s), the nanoridges appeared to be straighter.

Figure 8:
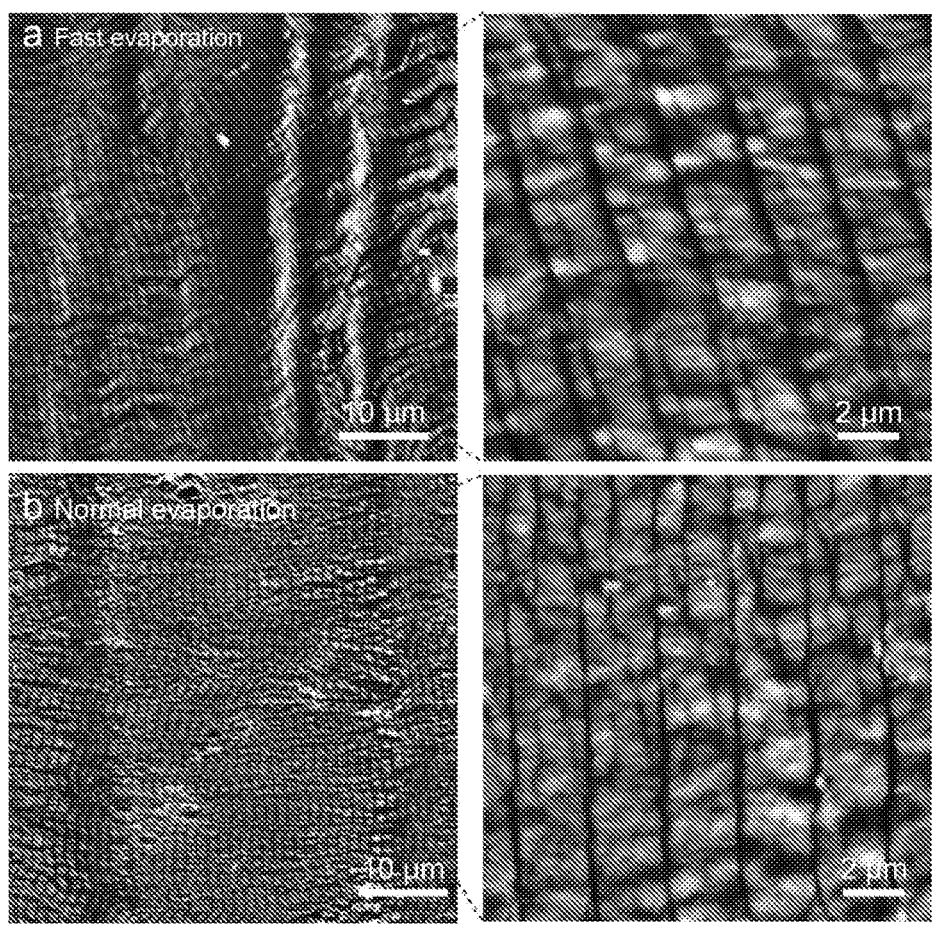
FIG. 8 shows surface morphologies of NiM structures assembled from wild-type M13 phages at different evaporation rates by the dip-pulling method of the present disclosure. The upper images (a) show two magnifications of a phage film structure formed under a fast evaporation rate in a chemical fume hood. The lower images (b) show two magnifications of a phage film structure formed under normal evaporation in room conditions. The method of claim 12, wherein the step of drawing the substrate occurs under room temperature conditions in a temperature range of about 20° C. to 25° C. Arrows indicate the microridge width $D_1$. Phage concentration was $1\times10^{14}$ pfu/ml. Pulling speed was 1.5 µm/s.

The effect of evaporation rates on the phage film formation was then investigated (FIG. 8). We found that the best evaporation condition for NiM structure formation was the normal room condition (FIG. 8b) at room temperature (RT). When the dip-pulling was operated inside a chemical fume hood to accelerate the evaporation, we found that the NiM structure was disturbed at the microscales (FIG. 8a). Compared to the normal room evaporation, the distribution of the microridges and microgrooves was not as uniform under the fast evaporation. Moreover, under the fast evaporation, microridge width $D_1$ significantly decreased. However, the nanoridge structures stayed the same under both evaporation conditions.

Figure 9:
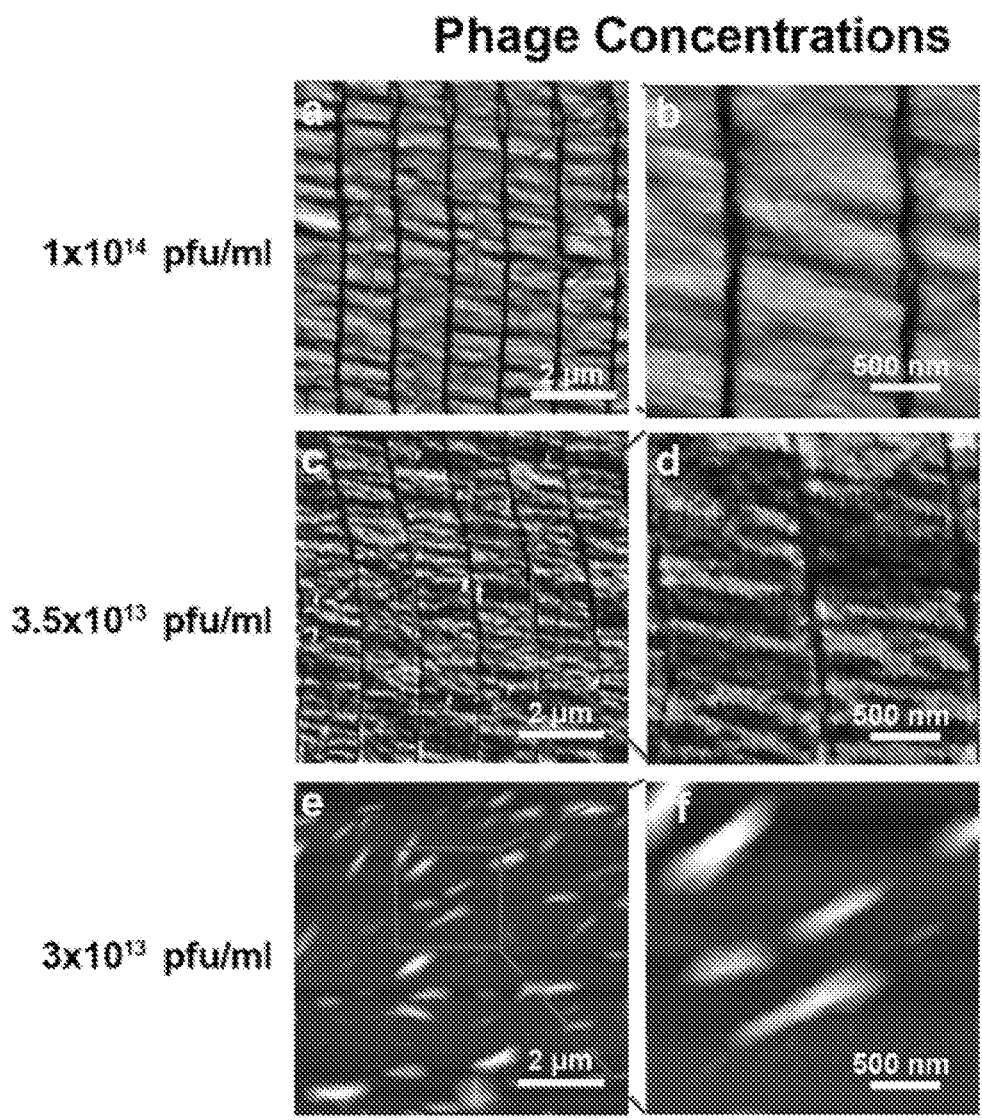
FIG. 9 shows surface morphologies of phage films assembled from wild-type M13 phages at different phage concentrations using the dip-pulling method of the present disclosure. The phages assembled into NiM patterns when the phage suspension concentration was at least $3.5\times10^{13}$ pfu/ml (a-d). Below this concentration, e.g., $3.5\times10^{13}$ pfu/ml (e,f) NiM patterns were not formed. Pulling speed, 1.5 µm/s.

We then studied the effect of the phage concentrations on the NiM structure formation (FIG. 9). Different concentrations of phage solutions, ranging from $1 \times 10^{13}$ pfu/ml to $2 \times 10^{14}$ pfu/ml, affected the phage film structures at a pulling speed of 1.5 μm/s. The concentration changes of the phage solutions didn't disturb the NiM structure and the six sizes parameters ($D_1$, $D_2$, $w_1$, $w_2$, $d_1$, $d_2$) when their concentration was at least $3.5 \times 10^{13}$ pfu/ml (FIG. 9a-d). However, in experiments when the phage concentration was below $3.5 \times 10^{13}$ pfu/ml, the NiM structure did not form (FIG. 9e-f).

Figure 10:
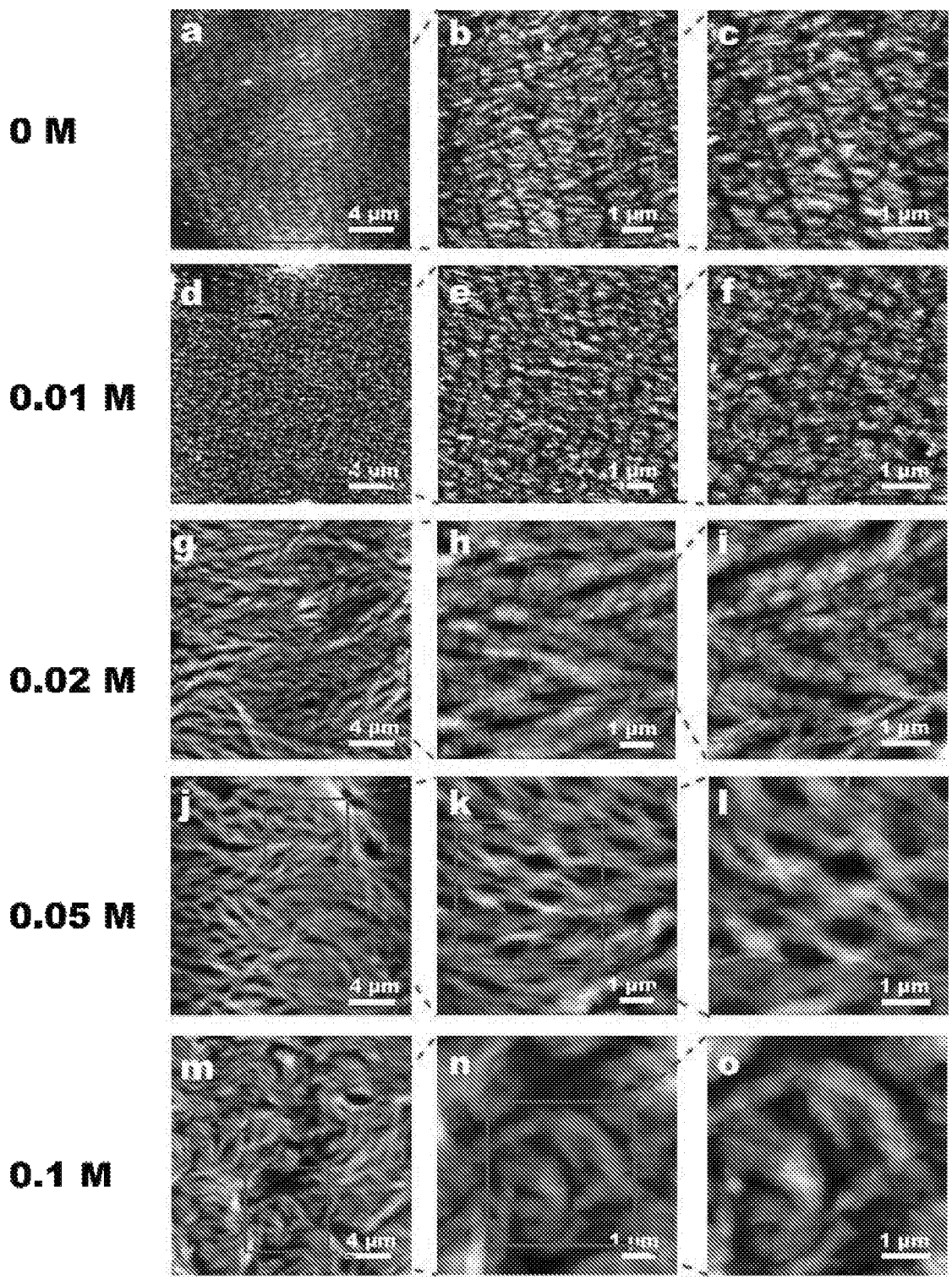
FIG. 10 shows micrographs of different magnifications of wild-type M13 phages which have self-assembled into films by the dip-pulling method under different salt (NaCl) concentrations (a-c: 0.0 M; d-f: 0.01 M; g-i: 0.02 M; j-l: 0.05 M; m-o: 0.1 M). The salt concentrations influenced the structure of the phage assemblies. When the salt concentration was greater than 0.01 M, the phage films assembled into a cross-linking pattern instead of the parallel-aligned NiM pattern. (Phage concentration, $7\times10^{13}$ pfu/ml; pulling speed, 1.5 µm/s).

To understand the effect of ionic strength on the formation of NiM structures, we studied the NiM structure formation under different NaCl concentrations in the phage solution with a particular phage concentration ($7 \times 10^{13}$ pfu/ml) and pulling speed (1.5 μm/s). We found that the NaCl concentrations significantly affected the NiM structure formation and generally lower NaCl concentrations benefited the formation of the NiM structures (FIG. 10a-f). When NaCl concentrations were higher than 0.01 M, phages did not assemble into NiM structures, but only formed non-parallel, crossed patterns. When the NaCl concentrations were increased from 0.02 to 0.05 M, the crossed patterns became more disordered (FIG. 10g-i). When the NaCl concentrations reached 0.1 M, the phages formed a completely disordered structure (FIG. 10m-o). Thus, overall a higher salt concentration tended to result in a more disordered phage film.

The effect of pH values of the phage solutions on the NiM structure formation when the salt concentration was 0.01 M, the phage concentration was $5 \times 10^{13}$ pfu/ml and the pulling speed was 1.5 μm/s, was investigated. The isoelectric point (pI) of M13 phage is 4.5. The pH of phage solutions was 7-8. Phages could stay in pH 3-11 for 20 min without losing their infectivity. Thus, we studied the effect of pH values when the pH values of the phage solutions were buffered from pH 3 to 11 (Table 1). When the pH value was between 6 to 11, NiM structures were still formed. When the pH value was higher than 11 or lower than 6, the NiM structures could not be formed.

Figure 11:
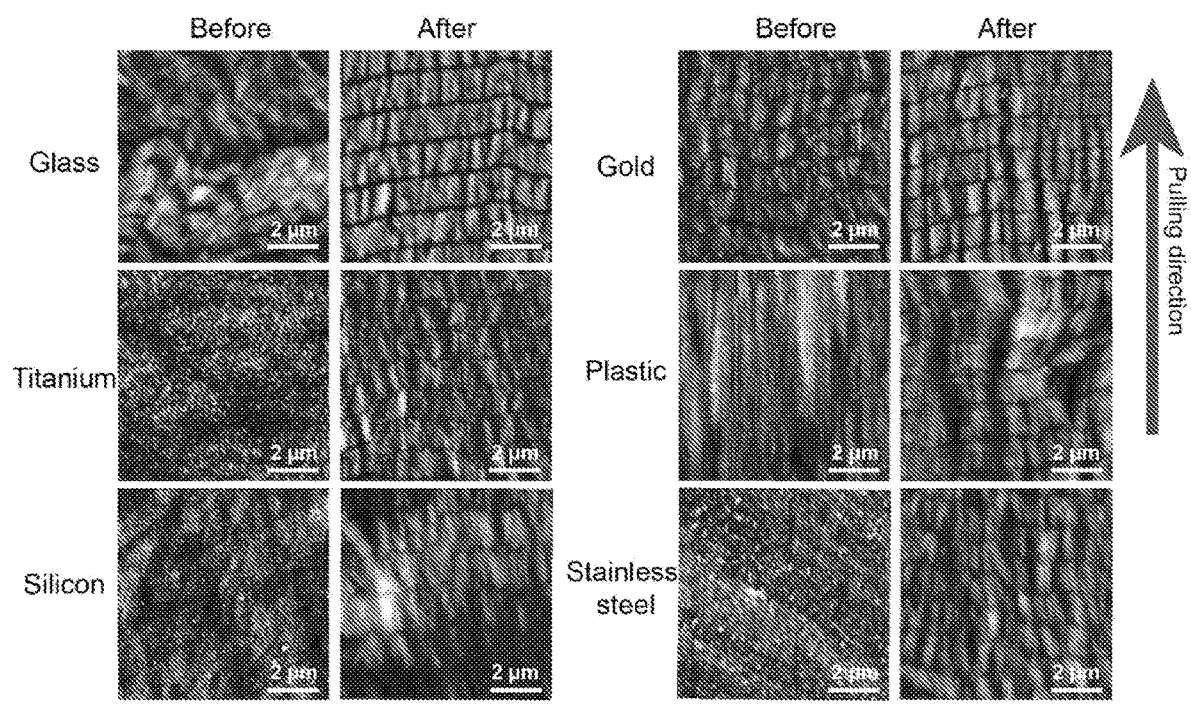
FIG. 11 shows M13 filamentous phage structures on a variety of substrates either without (before) or with (after) a polylysine coating on the substrate. On uncoated ("before") glass and gold substrates phages are assembled into nanoridges and nanogrooves with less organized structure, whereas no phages were found on uncoated titanium, silicon, plastic and stainless steel substrates. Highly ordered NiM structures were formed on all coated substrates. Arrow indicates the pulling direction.

The NiM structures of the present disclosure can be formed on a variety of substrates, including amorphous materials (e.g., glass and silicon oxide on a silicon wafer), crystalline inorganic materials (e.g., metals and metal alloys such as gold, titanium, and stainless steel), and organic materials (e.g., such as polymers and thermoplastics, e.g., polycarbonate plastics) (FIG. 11). The substrate can be rigid (e.g., glass, silicon, metal, plastic) or may be flexible (e.g., polymeric plastics). The substrate may have any desired shape, such as flat or curved, and may be a strip of material, or may have a convex or concave shape, or may be tubular. In at least certain embodiments, the substrate has been pre-treated to form a positively charged coating thereon, for example by treatment with polylysine. One or both surfaces of the substrate may be coated. For example, a tubular substrate may have a positively charged coated inner surface and a positively charged coated outer surface. NiM structures generally could not be formed on non-positively-charge coated substrates.

Further work was conducted to test the bidirectional differentiation of hiPSC-derived NPCs into neurons and astrocytes on the NiM structures using the following conditions: phage concentration, $1 \times 10^{14}$ pfu/ml; NaCl concentration, 0 M; pH, 7; pulling speed, 1.5 μm/s, to prepare phage films with the NiM structures of WT-phage or RGD-phage. Thus, we used three substrate groups, WT-phage, RGD-phage, and control (a polylysine-coated glass slide without phage), in the absence of differentiation inducers in the culture medium (non-differentiation medium).

Figure 12:
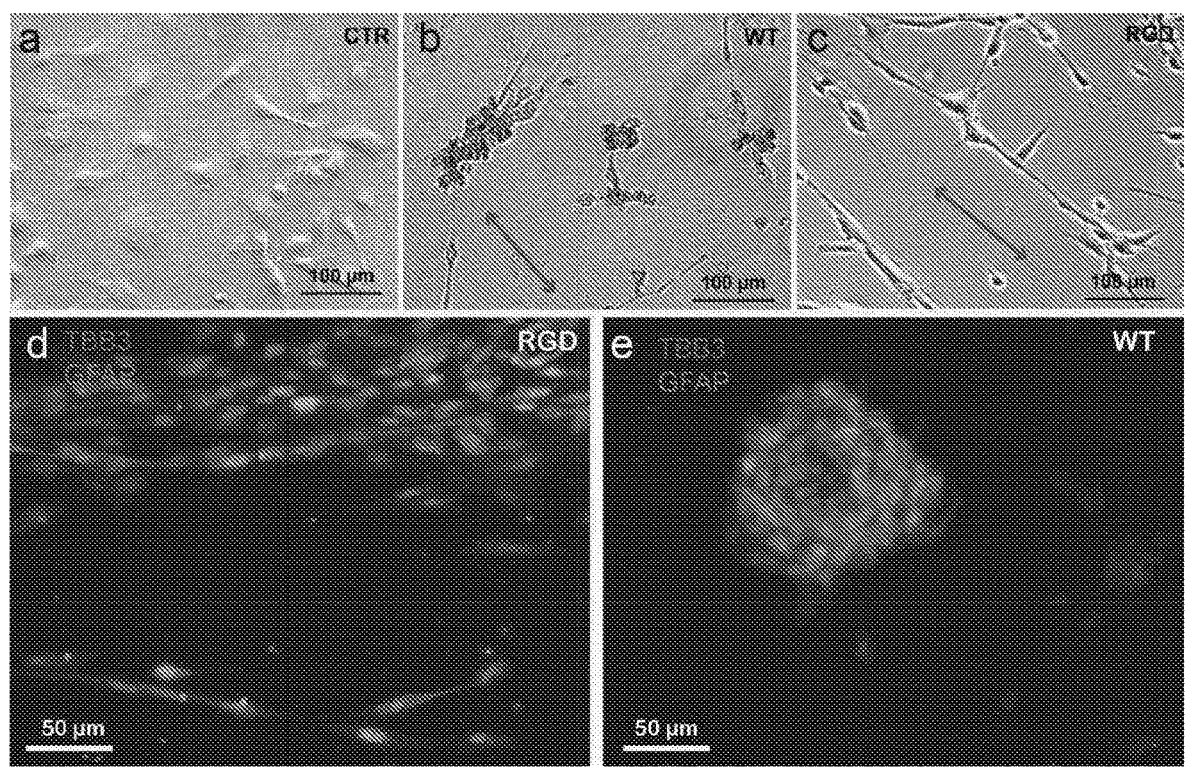
FIG. 12 shows micrographs of morphologies and bidirectional differentiation of cells on the different phage (control, WT, RGD) substrates formed under the same conditions (phage concentration, $1\times10^{14}$ pfu/ml; pulling speed, 1.5 µm/s.). HiPSC derived-NPCs were seeded onto different substrates, including WT phage films, RGD-phage films and bare control substrate (CTR, the polylysine-coated glass slides without phages). The three upper Images (a-c) are optical microscope images of the cultured cells on different substrates on Day 5. Compared to the control group (a), the cells grew on the phage films (b-c) showed different morphologies on Day 5. The NPCs were grown into clusters on WT phage films (b) but were aligned parallel to the microridge length direction on the RGD-phage films (c). Arrows denoted the microridge length direction. The NPCs on RGD-phage film (d) and WT phage film (e) were bidirectionally differentiated into neurons and astrocytes by phage films by Day 8. TBB3 is a neuron marker (red) and GFAP is an astrocyte marker (green).

The hiPSC-derived-NPCs were seeded on the three substrates in the non-differentiation medium. We observed obvious differences in cell morphology on different substrates. Starting from Day 2 after cell seeding, the cells on the control substrate were not elongated (FIG. 12a) but the cells on the two NiM structures showed an elongated morphology (FIG. 12 b-c). The elongated cells on the WT-phage film (FIG. 12b) trended to form clusters without preferential orientation, whereas those on the RGD-phage film, either isolated or clustered, were preferentially aligned along the length direction of microridges (FIG. 12c-d). Surprisingly, we found that the NiM structures of both RGD-phage and WT-phage could induce the bidirectional differentiation of NPCs into neurons and astrocytes (FIG. 12 d-e, respectively).

Figure 13A:
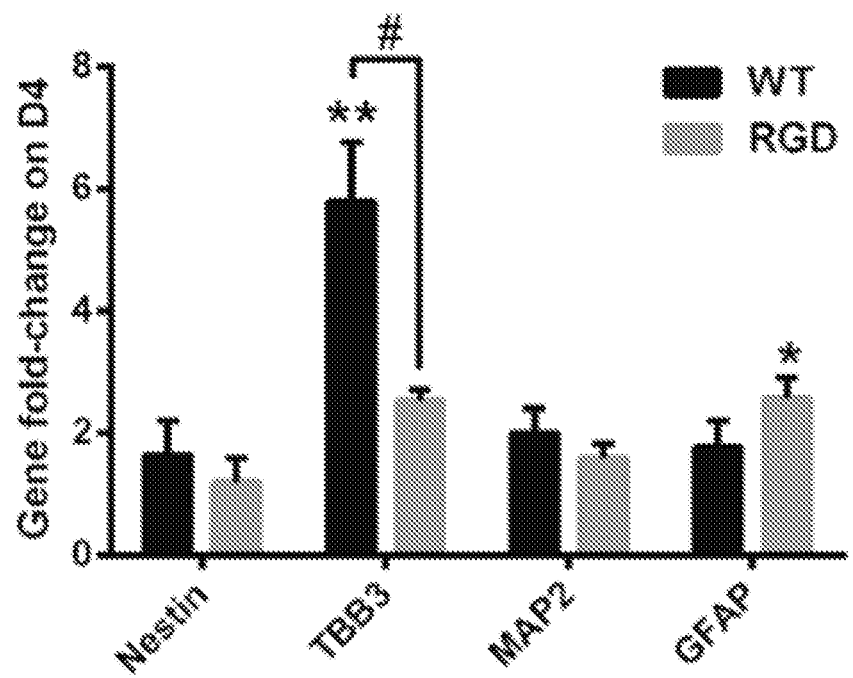
FIG. 13A shows neural differentiation after 4 days of neural progenitor cells (NPCs) on NiM structures of the present disclosure. Quantitation was by RT-qPCR or immunofluorescent intensity fold change of Nestin, marker for NPCs, TBB3 and MAP2, early and late stage markers for neurons, respectively, and GFAP, marker for astrocytes. The phage films were prepared by the dip-pulling method with Phage concentration=$1\times10^{14}$ pfu/ml and pulling speed=1.5 µm/s.). * or #, P≤0.05;  or ##, P≤0.01; * or ###, P≤0.001; **** or ####, P≤0.0001. * indicates the significant difference between WT/RGD and CTR, # indicates the significant difference between WT and RGD.
Figure 13B:
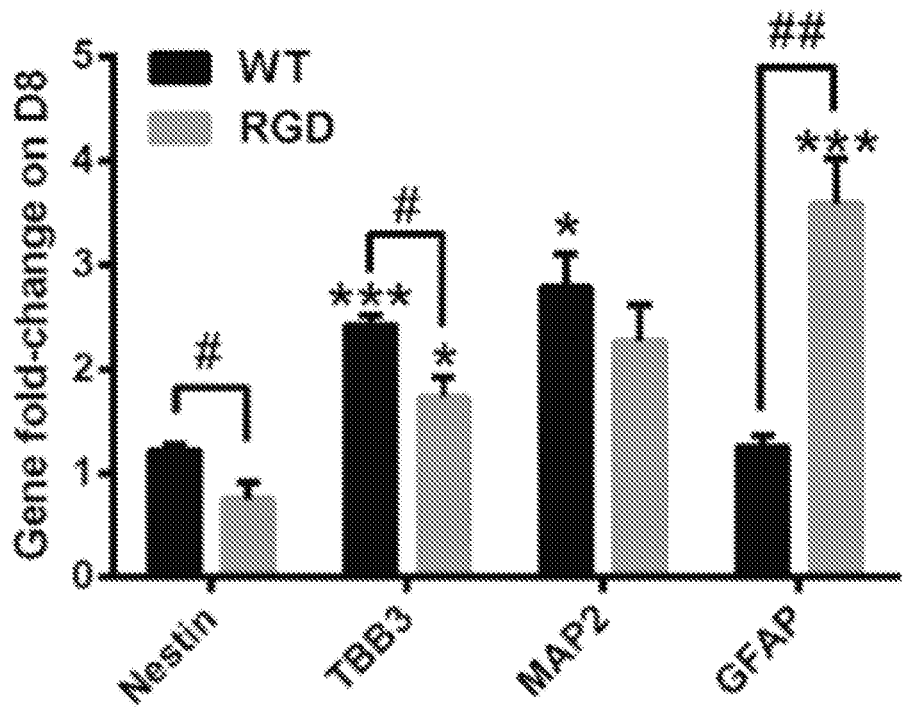
FIG. 13B shows neural differentiation after 8 days of neural progenitor cells (NPCs) on NiM structures of the present disclosure. Quantitation was by RT-qPCR or immunofluorescent intensity fold change of Nestin, marker for NPCs, TBB3 and MAP2, early and late stage markers for neurons, respectively, and GFAP, marker for astrocytes. The phage films were prepared by the dip-pulling method with Phage concentration=$1\times10^{14}$ pfu/ml and pulling speed=1.5 µm/s.). * or #, P≤0.05;  or ##, P≤0.01; * or ###, P≤0.001; **** or ####, P≤0.0001. * indicates the significant difference between WT/RGD and CTR, # indicates the significant difference between WT and RGD
Figure 13C:
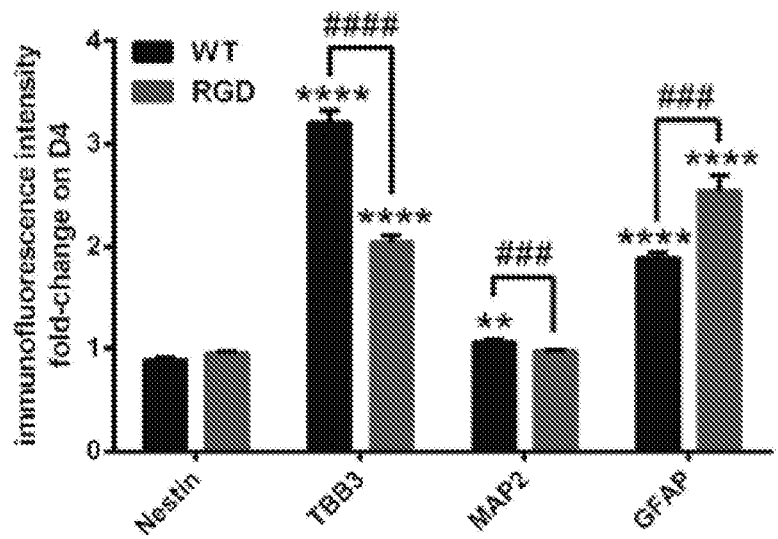
FIG. 13C shows neural differentiation after 4 days of neural progenitor cells (NPCs) on NiM structures of the present disclosure. Quantitation was by immunofluorescent intensity fold change of Nestin, marker for NPCs, TBB3 and MAP2, early and late stage markers for neurons, respectively, and GFAP, marker for astrocytes. Results are obtained by analysis of multiple immunofluorescence images for each marker using image J. The immuno-fluorescent intensity level of each marker in CTR (non-phage control group) were set to 1. The lefthand column for each marker indicates WT/CTR fluorescent intensity ratio and the righthand column for each marker indicates RGD/CTR fluorescent intensity ratio. The phage films were prepared by the dip-pulling method with Phage concentration=$1\times10^{14}$ pfu/ml and pulling speed=1.5 µm/s.). Scale bar: 100 µm. * or #, P≤0.05;  or ##, P≤0.01; * or ###, P≤0.001; **** or ####, P≤0.0001. * indicates the significant difference between WT/RGD and CTR, # indicates the significant difference between WT and RGD.
Figure 13D:
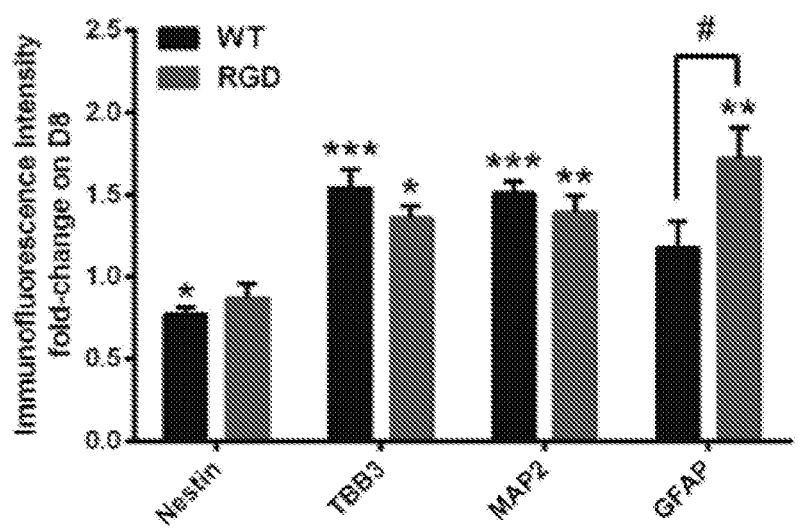
FIG. 13D shows neural differentiation after 8 days of neural progenitor cells (NPCs) on NiM structures of the present disclosure. Quantitation was by immunofluorescent intensity fold change of Nestin, marker for NPCs, TBB3 and MAP2, early and late stage markers for neurons, respectively, and GFAP, marker for astrocytes. Results are obtained by analysis of multiple immunofluorescence images for each marker using image J. The immuno-fluorescent intensity level of each marker in CTR (non-phage control group) were set to 1. The lefthand column for each marker indicates WT/CTR fluorescent intensity ratio and the righthand column for each marker indicates RGD/CTR fluorescent intensity ratio. The phage films were prepared by the dip-pulling method with Phage concentration=$1\times10^{14}$ pfu/ml and pulling speed=1.5 μm/s.). Scale bar: 100 μm. * or #, P≤0.05;  or ##, P≤0.01; * or ###, P≤0.001; **** or ####, P≤0.0001. * indicates the significant difference between WT/RGD and CTR, # indicates the significant difference between WT and RGD.

In order to verify that the NiM structures induced the intended bidirectional differentiation, we tested the possible neural differentiation of NPCs into neurons, astrocytes or oligodendrocytes by detecting their corresponding cellular markers. Nestin is an NPC marker, βIII-Tubulin (TBB3) and MAP2 are an early and late stage neuron marker, respectively. GFAP is an astrocyte marker. Olig2 is an oligodendrocyte marker. The mRNA and protein expression levels of the different markers for NPCs, neurons and astrocytes after 4 days and 8 days were tested by qRT-PCR (FIGS. 13A-13B) and immunofluorescent intensity fold change (FIGS. 13C-13D), respectively, on the cells cultured on the phage groups. FIGS. 13C-D were generated by analysis of multiple immunofluorescence images for each marker using image J. Results in FIGS. 13A-D were normalized to those of the control group.

In general, cells on the WT-phage films showed a higher expression level of TBB3 and MAP2 (neuron) markers, while the cells on the RGD-phage films showed a higher expression level of GFAP indicating a greater percentage of astrocytes. NPC markers for all groups were detected compared to the control group, we could detect a significantly high level of the makers for both neurons and astrocytes, but could not detect the marker for oligodendrocytes (Olig2), indicating that the phage films could only induce hiPSC-derived-NPCs to differentiate into neurons and astrocytes, not oligodendrocytes. Moreover, at the two time points, the cells on the WT phage films showed a higher expression level of the early stage (TBB3) and late stage (MAP2) neuron markers than those on the RGD-phage films at the both mRNA and protein level (FIGS. 13A-D). On the other hand, at both time points, the cells on the RGD-phage films presented a higher expression level of astrocyte marker (GFAP) than those on the WT-phage films. Therefore, although both WT-phage and RGD-phage films induced the bidirectional differentiation of NPCs into both neurons and astrocytes, the WT-phage films appeared to favor differentiation into neurons while RGD-phage films appeared to favor differentiation into astrocytes. On Day 4, the expression level of the NPC marker (Nestin) was similar in each group, but the expression level of TBB3 and GFAP was significantly increased in both WT-phage and RGD-phage film groups compared to the control group. Compared to the control group, the cells on the WT-phage film expressed a 3.2-fold and 1.9-fold higher fluorescent intensity of TBB3 and GFAP, respectively, while those on the RGD phage film showed a 2-fold and 2.5-fold fluorescent intensity increase in TBB3 and GFAP, respectively. On Day 4, the cells on the WT-phage films showed 5-fold higher mRNA expression of TBB3 than the control group These results collectively indicated that the unique phage film structure could induce bidirectional differentiation of hiPSC s-derived NPCs within 4 days (FIGS. 13A,13C). From Day 4 to Day 8, the level of TBB3 expression dropped, but the level of MAP2 expression increased, indicating that the neurons were mature within 8 days (FIGS. 13B,13D), vs the 2 weeks usually required for NPCs to become mature neurons. The presently disclosed NiM structures achieved the differentiation of NPCs into mature neurons in 8 days, indicating that the novel NiM structures disclosed herein could guide and accelerate the neuron maturation of the hiPSC-derived NPCs due to their unique nanotopographies, even without differentiation inducers in the culture medium. Further, generation of astrocytes from NPCs or NSCs by using astrocyte induction medium usually needs more than 30 days. Thus, the novel NiM structures disclosed herein substantially shortened the neural differentiation duration.

Figure 14A:
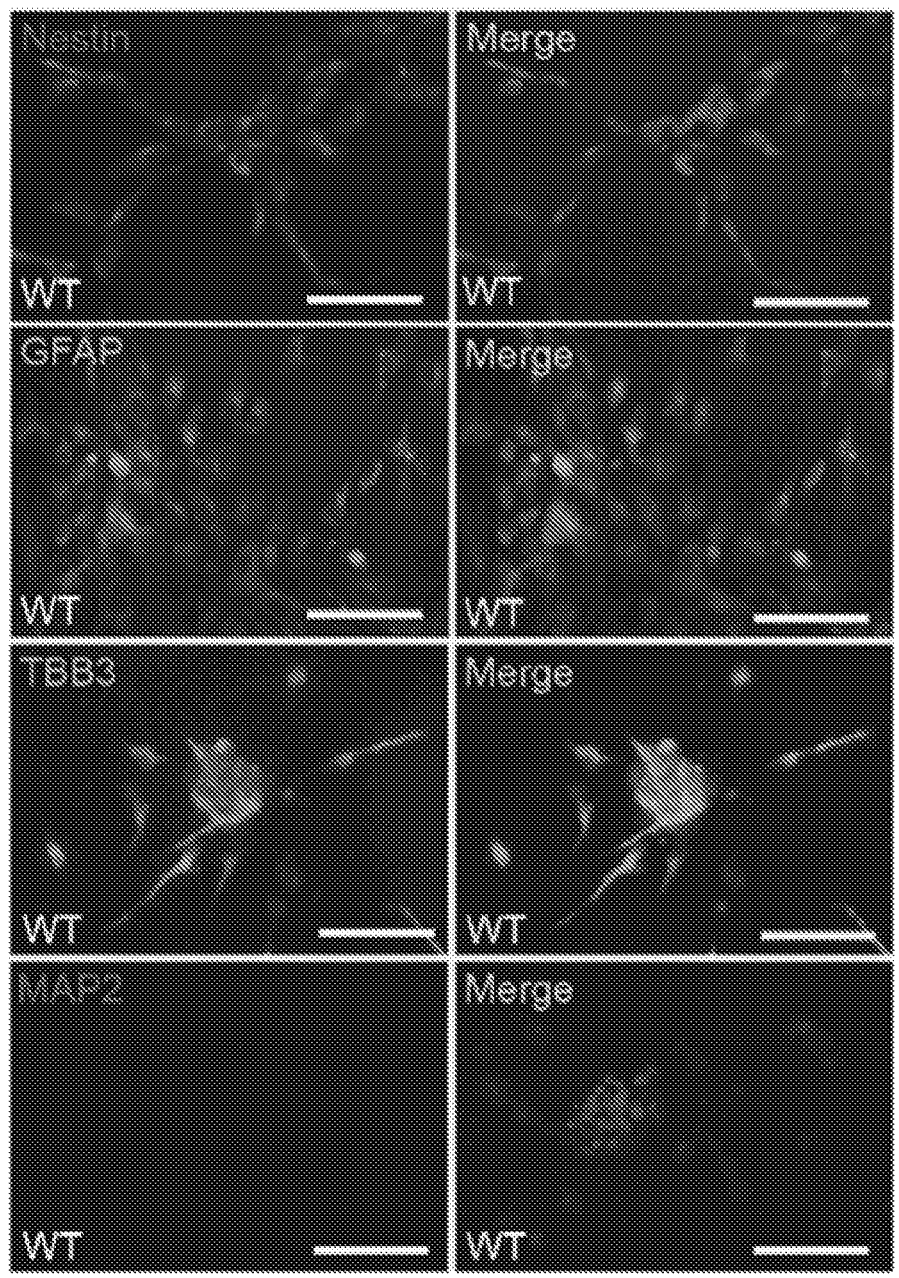
FIG. 14A shows immunofluorescence imaging results on day 4 for Nestin, TBB3, MAP2, and GFAP, markers for the neural differentiation of the NPCs cultured on WT phage NiM structures. Scale bar: 100 μm.
Figure 14B:
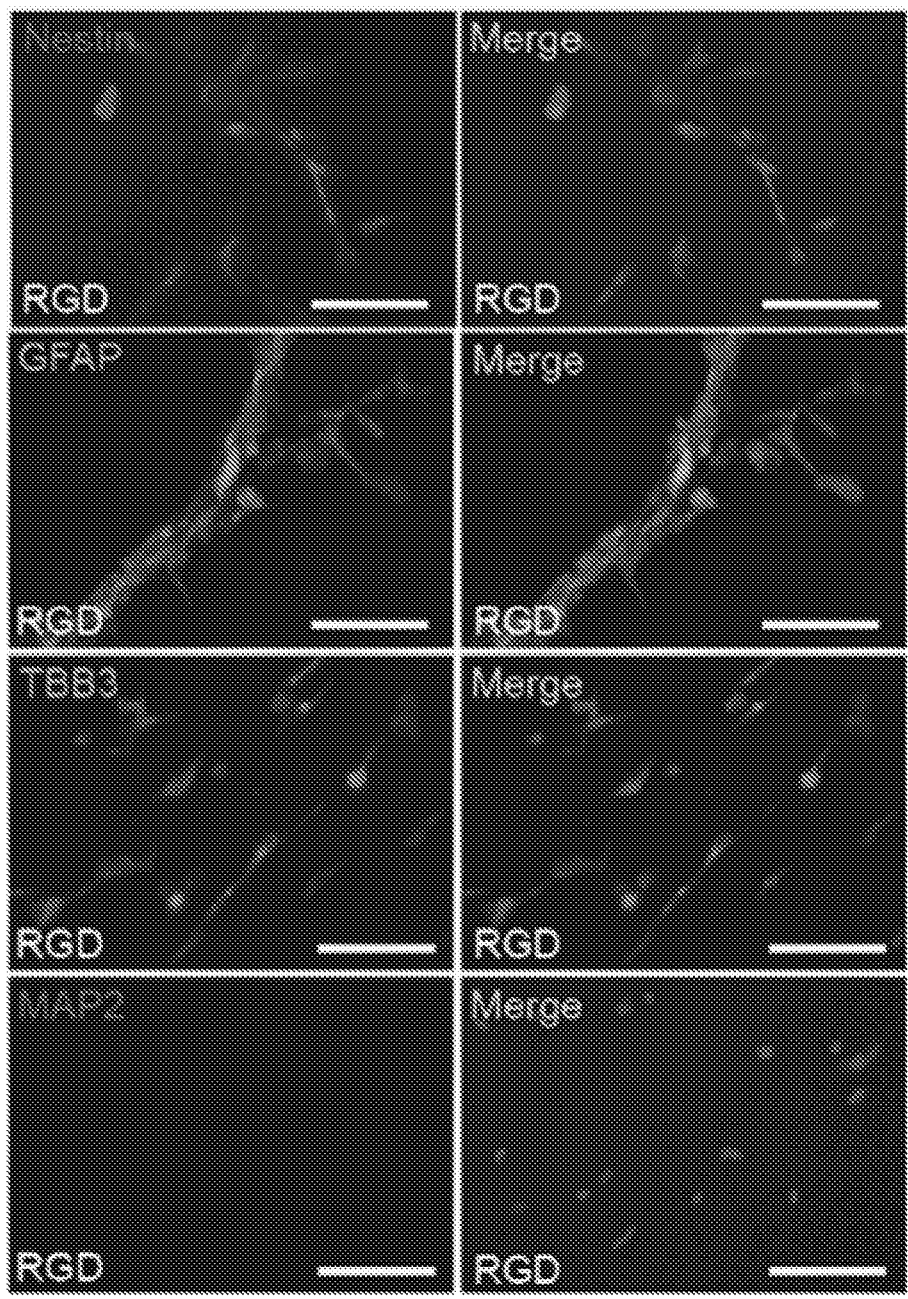
FIG. 14B shows immunofluorescence imaging results on day 4 for Nestin, TBB3, MAP2, and GFAP, markers for the neural differentiation of the NPCs cultured on RGD phage NiM structures. Scale bar: 100 μm.
Figure 14C:
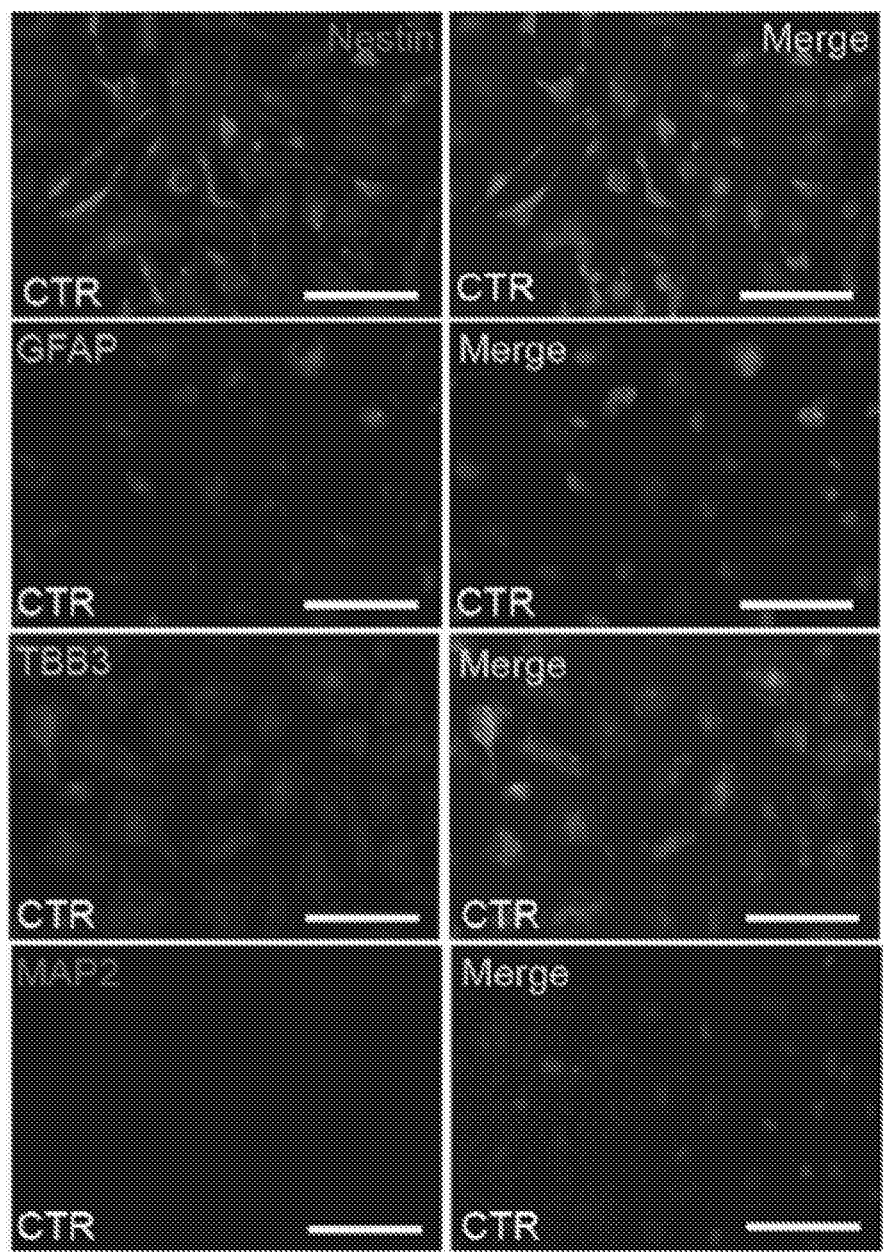
FIG. 14C shows immunofluorescence imaging results on day 4 for Nestin, TBB3, MAP2, and GFAP, markers for the neural differentiation of the NPCs cultured on polylysine-coated substrates for use as a control against the results of FIGS. 14A-B. Scale bar: 100 μm.

FIG. 14 shows immunofluorescence imaging results of the markers for the neural differentiation of the NPCs on Day 4. Cells on the WT phage films had a higher expression level of TBB3 (neuron) marker, while those on the RGD-phage films showed a higher expression level of GFAP (astrocyte) marker. These results indicate that WT-phage and RGD-phage films more efficiently induced the differentiation of NPCs into neurons and astrocytes, respectively. These results were confirmed with similar imaging results on Day 8 (see FIG. 7e in U.S. Provisional Patent Application Ser. No. 62/832,954, filed on Apr. 12, 2019).

Figure 15:
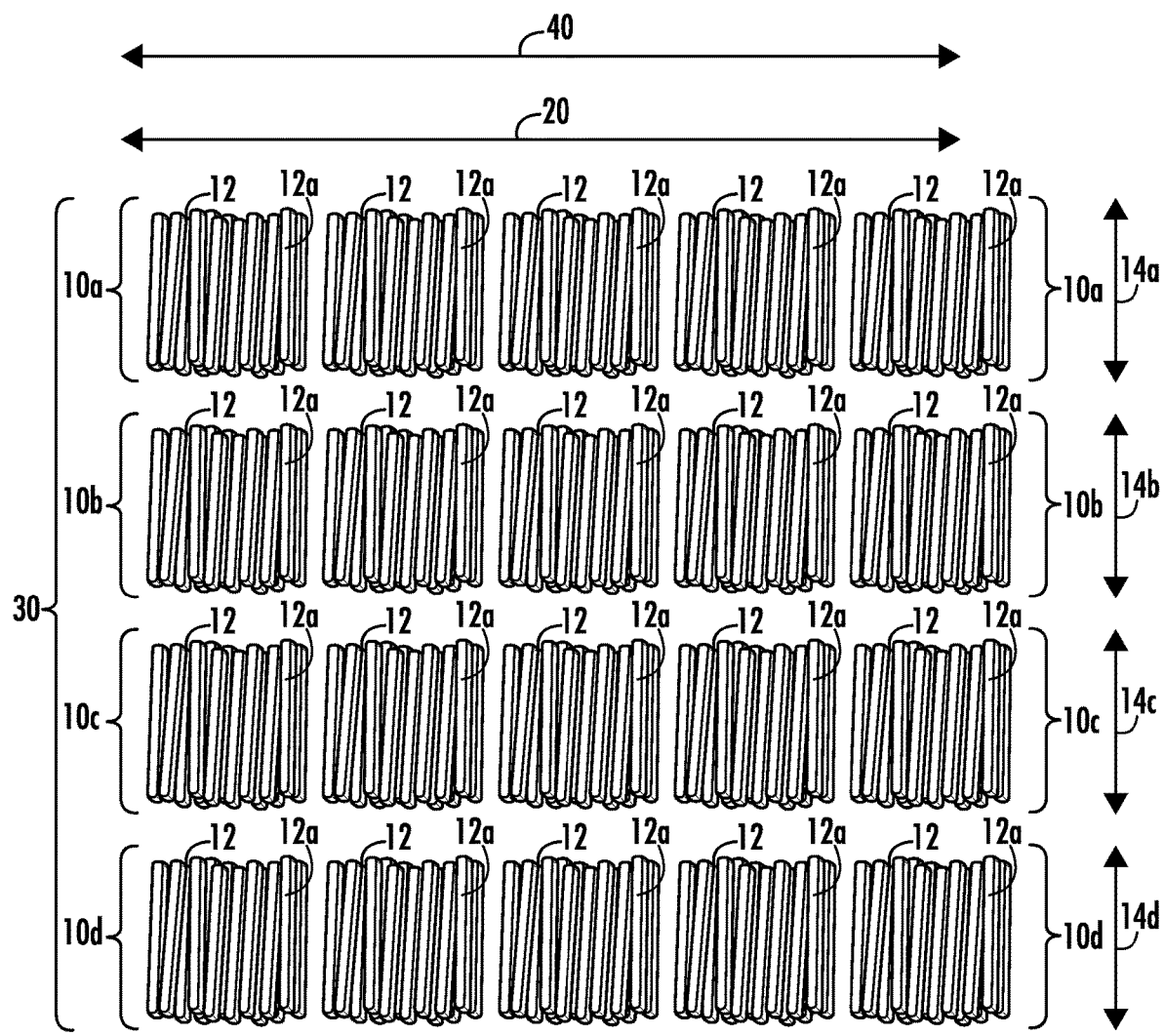
FIG. 15 is a schematic showing a portion of a microridge made up of lines of nanoridges and the longitudinal axes thereof.

FIG. 15 shows a schematic representation of a microridge 30 and several parallel lines of nanoridges 10a, 10b, 10c, and 10d which make up the microridge 30. Each line of nanoridges 10a, 10b, 10c, and 10d is made up of a plurality of nanoridges 12. Each line of nanoridges 10a, 10b, 10c, and 10d has a longitudinal axis 20. The microridge 30 has a longitudinal axis 40. As discussed in further detail earlier, each nanoridge 12 is comprised of a plurality (bundle) of substantially parallel nanofibers 12a with a longitudinal axis. For example, the nanofibers 12a of nanoridges 12 in line of nanoridges 10a have an averaged longitudinal axis 14a, the nanofibers 12a of nanoridges 12 in line of nanoridges 10b have an averaged longitudinal axis 14b, the nanofibers 12a of nanoridges 12 in line of nanoridges 10c have an averaged longitudinal axis 14c, the nanofibers 12a of nanoridges 12 in line of nanoridges 10d have an averaged longitudinal axis 14d. The longitudinal axis 20 of each line of nanoridges 10a, 10b, 10c, and 10d is substantially parallel to the longitudinal axis 40 of the microridge 30, and the longitudinal axes 14a, 14b, 14c, and 14d of the nanofibers 12a of the nanoridges 12 are substantially perpendicular to the longitudinal axis 40 of microridge 30 and to the longitudinal axes 20 of the lines of nanoridges 10a, 10b, 10c, and 10d.

In summary, the present disclosure is directed in last least one embodiment, to a phage structure, comprising a substrate having a positively-charged surface, the surface having an ordered arrangement of parallel microridges thereon, each microridge comprising a plurality of nanoridges and having a longitudinal axis, wherein each nanoridge comprises a bundle of phage nanofibers having longitudinal axes, the phage nanofibers within a single bundle are arranged in a smectic alignment such that the longitudinal axes of the phage nanofibers of a given bundle substantially parallel to one another and are substantially parallel to the longitudinal axes of phage nanofibers in adjacent nanoridges, and wherein the longitudinal axis of each microridge is substantially perpendicular to the longitudinal axes of the phage nanofibers which comprise the nanoridges of the microridge. The microridges of the phage structure may be separated by microvalleys comprising nanoridges having lesser thicknesses than those of the nanoridges in the microridges. The nanoridges of the microridge of the phage structure may be are arranged in a plurality of parallel lines, and wherein each line of nanoridges has a longitudinal axis that is parallel to the longitudinal axis of the microridge comprising the nanoridges. The substrate of the phage structure may be selected from glass, silicon dioxide, silicon oxide on a silicon wafer, metals, metal alloys, oxides, organic surfaces, plastics, and polymers. The phage nanofibers of the phage structure may be selected from the group consisting of M13, f1, and fd phages. The phage nanofibers of the phage structure may display cell adhesion peptides. The phage structure may have a laminin coating thereon.

In another embodiment, the present disclosure is directed to a method of inducing differentiation in stem cells, comprising (1) providing a phage structure, comprising a substrate having a positively-charged surface, the surface having an ordered arrangement of parallel microridges thereon, each microridge comprising a plurality of nanoridges and having a longitudinal axis, wherein each nanoridge comprises a bundle of phage nanofibers having longitudinal axes, the phage nanofibers in each bundle arranged in a smectic alignment such that the longitudinal axes of the phage nanofibers within a single bundle are substantially parallel to one another and are substantially parallel to the longitudinal axes of phage nanofibers in adjacent nanoridges, and wherein the longitudinal axis of each microridge is substantially perpendicular to the longitudinal axes of the phage nanofibers which comprise the nanoridges of the microridge, (2) disposing stem cells on the phage structure under growth conditions comprising a growth medium, and (3) culturing the stem cells to a form a culture of differentiated stem cells. The stem cells may be obtained from induced pluripotent stem cells. The stem cells may be neural progenitor cells (NPCs). The NPCs may be induced to differentiate into neurons and astrocytes. The phage structure used in the method may comprise any one or more of the features described above.

In another embodiment, the present disclosure is directed to a method of making a phage structure, comprising (1) providing a substrate having a positively-charged surface, (2) dipping the substrate into a phage suspension comprising phage nanofibers, and (3) drawing the substrate in a pulling direction out of the phage suspension at a pull speed such that the phage nanofibers adhere to the substrate surface in an ordered arrangement, wherein the ordered arrangement comprises a plurality of parallel microridges on the substrate surface, each microridge comprising a plurality of nanoridges and having a longitudinal axis, and wherein each nanoridge comprises a bundle of phage nanofibers having longitudinal axes, the phage nanofibers within in each bundle arranged in a smectic alignment such that the longitudinal axes of the phage nanofibers within a single bundle are substantially parallel to one another and are substantially parallel to the longitudinal axes of phage nanofibers in adjacent nanoridges, and wherein the longitudinal axis of each microridge is substantially perpendicular to the longitudinal axes of the phage nanofibers which comprise the nanoridges of the microridge. The longitudinal orientation of the microridges may be perpendicular to the pulling direction. The phage suspension may have a concentration of at least at least $3.5 \times 10^{13}$ pfu/ml. The phage suspension may have a salt concentration in a range of about 0.01 M to 0.0. M. The phage suspension may have a pH in a range of about 6 to about 11. The step of drawing the substrate may occur under room temperature conditions in a temperature range of about 20° C. to about 25° C. The phage structure made in the method may comprise any one or more of the features described above.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the various components and compositions described herein, the methods described herein or in the steps or the sequence of steps of the methods described herein without departing from the spirit and scope of the present disclosure.

What is claimed is:

1. A phage structure, comprising a substrate having a positively charged surface, the surface having an ordered arrangement of parallel microridges thereon, each microridge comprising a plurality of nanoridges and having a longitudinal axis, wherein each nanoridge comprises a bundle of phage nanofibers having longitudinal axes, the phage nanofibers within a single bundle are arranged in a smectic alignment such that the longitudinal axes of the phage nanofibers of a given bundle are substantially parallel to one another and are substantially parallel to the longitudinal axes of phage nanofibers in adjacent nanoridges, and wherein the longitudinal axis of each microridge is substantially perpendicular to the longitudinal axes of the phage nanofibers which comprise the nanoridges of the microridge.

2. The phage structure of claim 1, wherein the microridges are separated by microvalleys comprising nanoridges having lesser thicknesses than those of the nanoridges in the microridges.

3. The phage structure of claim 1, wherein the nanoridges of the microridge are arranged in a plurality of parallel lines, and wherein each line of nanoridges has a longitudinal axis that is parallel to the longitudinal axis of the microridge comprising the nanoridges.

4. The phage structure of claim 1, wherein the substrate is selected from glass, silicon dioxide, silicon oxide on a silicon wafer, metals, metal alloys, oxides, organic surfaces, plastics, and polymers.

5. The phage structure of claim 1, wherein the phage nanofibers are selected from the group consisting of M13, f1, and fd phages.

6. The phage structure of claim 1, wherein the phage nanofibers display cell adhesion peptides.

7. The phage structure of claim 1, comprising a laminin coating thereon.

8. A method of inducing differentiation in stem cells, comprising
providing a phage structure, comprising a substrate having a positively charged surface, the surface having an ordered arrangement of parallel microridges thereon, each microridge comprising a plurality of nanoridges and having a longitudinal axis, wherein each nanoridge comprises a bundle of phage nanofibers having longitudinal axes, the phage nanofibers in each bundle arranged in a smectic alignment such that the longitudinal axes of the phage nanofibers within a single bundle are substantially parallel to one another and are substantially parallel to the longitudinal axes of phage nanofibers in adjacent nanoridges, and wherein the longitudinal axis of each microridge is substantially perpendicular to the longitudinal axes of the phage nanofibers which comprise the nanoridges of the microridge;
disposing stem cells on the phage structure under growth conditions comprising a growth medium; and
culturing the stem cells to a form a culture of differentiated stem cells.

9. The method of claim 8, wherein the stem cells are obtained from induced pluripotent stem cells.

10. The method of claim 8, wherein the stem cells are neural progenitor cells (NPCs).

11. The method of claim 10, wherein the NPCs are induced to differentiate into neurons and astrocytes.

12. A method of making a phage structure, comprising:
providing a substrate having a positively charged surface;
dipping the substrate into a phage suspension comprising phage nanofibers;
drawing the substrate in a pulling direction out of the phage suspension at a pull speed such that the phage nanofibers adhere to the substrate surface in an ordered arrangement, wherein the ordered arrangement comprises a plurality of parallel microridges on the substrate surface, each microridge comprising a plurality of nanoridges and having a longitudinal axis, and wherein each nanoridge comprises a bundle of phage nanofibers having longitudinal axes, the phage nanofibers within in each bundle arranged in a smectic alignment such that the longitudinal axes of the phage nanofibers within a single bundle are substantially parallel to one another and are substantially parallel to the longitudinal axes of phage nanofibers in adjacent nanoridges, and wherein the longitudinal axis of each microridge is substantially perpendicular to the longitudinal axes of the phage nanofibers which comprise the nanoridges of the microridge.

13. The method of claim 12, wherein the longitudinal orientation of the microridges is perpendicular to the pulling direction.

14. The method of claim 12, wherein the phage suspension has a concentration of at least at least $3.5 \times 10^{13}$ pfu/ml.

15. The method of claim 12, wherein the phage suspension has a salt concentration in a range of about 0.01 M to 0.0 M.

16. The method of claim 12, wherein the phage suspension has a pH in a range of about 6 to about 11.

17. The method of claim 12, wherein the step of drawing the substrate occurs under room temperature conditions in a temperature range of about 20° C. to about 25° C.

* * * * *